United States Patent
Teh et al.

(10) Patent No.: US 8,133,686 B2
(45) Date of Patent: Mar. 13, 2012

(54) IL-8 AS A BIOMARKER FOR SUNITINIB RESISTANCE

(75) Inventors: Bin Tean Teh, Grand Rapids, MI (US); Dan Huang, Ada, MI (US); Kyle Furge, Kalamazoo, MI (US); Richard Kahnoski, Grand Rapids, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 173 days.

(21) Appl. No.: 12/466,951

(22) Filed: May 15, 2009

(65) Prior Publication Data

US 2009/0285832 A1    Nov. 19, 2009

Related U.S. Application Data

(60) Provisional application No. 61/053,628, filed on May 15, 2008.

(51) Int. Cl.
 G01N 33/53   (2006.01)
 G01N 33/574   (2006.01)
 C12Q 1/68   (2006.01)
(52) U.S. Cl. .............................. 435/7.1; 435/6; 435/7.23
(58) Field of Classification Search .................. None
 See application file for complete search history.

(56) References Cited

FOREIGN PATENT DOCUMENTS

WO   WO 2006/066071   *   6/2006

OTHER PUBLICATIONS

Brat, D.J., et al. The role of interleukin-8 and its receptors in gliomagenesis and tumoral angiogenesis. Neuro-oncol 7, 122-133 (2005).
Collins, R.J., et al. Internucleosomal DNA cleavage should not be the sole criterion for identifying apoptosis. International Journal of Radiation Biology 61, 451-453 (1992).
De Mulder, P.H., et al. Angiogenesis inhibitors for the systemic treatment of metastatic renal cell carcinoma: sunitinib, sorafenib, bevacizumab and temsirolimus. Ned Tijdschr Geneeskd 152, 371-375 (2008).
Escudier, B., et al. Sorafenib in advanced clear-cell renal-cell carcinoma. N Engl J Med 356, 125-134 (2007).
Faivre, S., et al. Safety, pharmacokinetic, and antitumor activity of SU11248, a novel oral multitarget tyrosine kinase inhibitor, in patients with cancer. J Clin Oncol 24, 25-35 (2006).
Furge, K.A., et al. Detection of DNA copy number changes and oncogenic signaling abnormalities from gene expression data reveals MYC activation in high-grade papillary renal cell carcinoma. Cancer Res 67, 3171-3176 (2007).
Gold, R., et al. Differentiation between cellular apoptosis and necrosis by the combined use of in situ tailing and nick translation techniques. Laboratory investigation; a journal of technical methods and pathology 71, 219-225 (1994).
Greenman, C., et al. Patterns of somatic mutation in human cancer genomes. Nature 446, 153-158 (2007).
Hanahan, D. & Weinberg, R.A. The hallmarks of cancer. Cell 100, 57-70 (2000).
Huang, D., et al. Inhibition of MAPK kinase signaling pathways suppressed renal cell carcinoma growth and angiogenesis in vivo. Cancer Res 68, 81-88 (2008).
Jemal, A., et al. Cancer statistics, 2008. CA Cancer J Clin 58, 71-96 (2008).
Kane, R.C., et al. Sorafenib for the treatment of advanced renal cell carcinoma. Clin Cancer Res 12, 7271-7278 (2006).
Koch, A.E., et al. Interleukin-8 as a macrophage-derived mediator of angiogenesis. Science 258, 1798-1801 (1992).
Mendel, D.B., et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9, 327-337 (2003).
Mizukami, Y., et al. Induction of interleukin-8 preserves the angiogenic response in HIF-1alpha-deficient colon cancer cells. Nat Med 11, 992-997 (2005).
Murphy, D.A., et al. Inhibition of tumor endothelial ERK activation, angiogenesis, and tumor growth by sorafenib (BAY43-9006). The American journal of pathology 169, 1875-1885 (2006).
O'Farrell, A.M., et al. An innovative phase I clinical study demonstrates inhibition of FLT3 phosphorylation by SU11248 in acute myeloid leukemia patients. Clin Cancer Res 9, 5465-5476 (2003).
O'Farrell, A.M., et al. SU11248 is a novel FLT3 tyrosine kinase inhibitor with potent activity in vitro and in vivo. Blood 101, 3597-3605 (2003).
Osusky, K.L., et al. The receptor tyrosine kinase inhibitor SU11248 impedes endothelial cell migration, tubule formation, and blood vessel formation in vivo, but has little effect on existing tumor vessels. Angiogenesis 7, 225-233 (2004).
Rini, B.I. Temsirolimus, an inhibitor of mammalian target of rapamycin. Clin Cancer Res 14, 1286-1290 (2008).
Rock, E.P., et al. Food and Drug Administration drug approval summary: Sunitinib malate for the treatment of gastrointestinal stromal tumor and advanced renal cell carcinoma. Oncologist 12, 107-113 (2007).
Schlessinger, J. Cell signaling by receptor tyrosine kinases. Cell 103, 211-225 (2000).
Schueneman, A.J., et al. SU11248 maintenance therapy prevents tumor regrowth after fractionated irradiation of murine tumor models. Cancer Res 63, 4009-4016 (2003).
Smith, D.R., et al. Inhibition of interleukin 8 attenuates angiogenesis in bronchogenic carcinoma. J Exp Med 179, 1409-1415 (1994).

* cited by examiner

*Primary Examiner* — Laura B Goddard
(74) *Attorney, Agent, or Firm* — Honigman Miller Schwartz and Cohn LLP; Douglas H. Siegel

(57) ABSTRACT

A method of determining whether a tumor will be non-responsive to sunitinib therapy including detecting whether IL-8 or MMP12 expression levels in the tumor are elevated as compared to a control, that is, a tumor having elevated IL-8 or MMP12 levels will be non-responsive to sunitinib. Also, a method for inhibiting the proliferation or causing the death of a sunitinib-resistant tumor cell by contacting the cell with an agent that inhibits IL-8 or MMP12 activity and with sunitinib, whereby proliferation of the tumor cell is inhibited or the tumor cell dies. Further, the invention includes compositions and kits that include an IL-8 inhibitor or an MMP12 inhibitor and sunitinib, and related methods of treatment.

6 Claims, 23 Drawing Sheets

C

D

E

IL-8 AS A BIOMARKER FOR SUNITINIB RESISTANCE

CROSS REFERENCE TO RELATED APPLICATION

This application claims the benefit of an invention which was disclosed in U.S. Provisional Application 61/053,628 filed May 15, 2008, entitled "Methods for Determining Responsiveness to Renal Cell Carcinoma Therapy and Related Methods, Markers, and Targets and the aforementioned application is incorporated herein by reference in its entirety.

FIELD OF INVENTION

This invention is in the field of molecular biology and medicine and, more specifically, relates to cancer treatments and biomarkers for cancer therapy.

BACKGROUND OF THE INVENTION

Renal cell carcinoma (RCC) arises in the renal cortex and comprises 80-85% of all kidney cancers. Although it only accounts for about 2% of all cancers, the incidence of kidney malignancies has increased over the past three decades. There will be approximately 54,390 newly diagnosed kidney cancer cases and 13,010 estimated deaths in the United States in 2008.1 RCC is refractory to chemotherapy and radiotherapy. Immnotherapy with IFN or high-dose IL-2 have only a 10-20% response rate and are often accompanied by severe side effects. Until recently, three targeted therapeutics, temsirolimus (TORISEL®), sunitinib (SUTENT®), and sorafenib (NEXAVAR®), which target mammalian target of rapamycin (mTOR), receptor tyrosine kinases (RTKs) and Raf kinases, respectively, have been approved to treat advanced human clear cell RCC (ccRCC).2-6

About a forty percent (40%) response rate was achieved in clinical trials for sunitinib ("SU11248"). SU11248 is an orally-available small molecule inhibitor of several class III and class V split-kinase domain receptor tyrosine kinases (RTKs), including VEGFR, PDGFR, FLT3, c-KIT, and RET. SU11248 was approved to treat advanced human ccRCC in 2006, but the mechanism of action is unknown. Moreover, after about one year of treatment, almost all patients develop resistance to SU11248; and the mechanism of resistance also is unknown.

SUMMARY OF THE INVENTION

The PDGFR signaling pathway could be fully activated and inhibited by SU11248. But the activation of PDGFR signaling pathway alone could not stimulate the growth of RCC cells in vitro; neither did SU11248 inhibit the proliferation of RCC cells when PDGFR pathway was suppressed. VEGFR signaling pathways could be activated and promote the proliferation of endothelial cells. Both effects could be inhibited by SU11248 in vitro. In vivo, SU11248 caused growth inhibition or regression of RCC xenograft tumors. This dramatic effect was mainly mediated by the disruption of tumor vasculature, accompanied by the inhibition of the release of IL-8 in the plasma. Resistance to SU11248 also was mimiced in xenograft models. Compared to SU11248-sensitive samples, there were higher MVDs in the resistant tumors, which indicated an angiogenesis escape had occurred in SU11248-resistant RCC. Neutralization of IL-8 activity resensitized resistant RCC tumor to SU11248 treatment, indicating IL-8 functionally contributed to SU11248 resistance. Elevation of the IL-8 gene expression also was found in RCC patients who showed no response to SU11248. Importantly, the inventors found IL-8 gene expression could predict the resistant phenotype for RCC patients; and a sunitinib-resistant cancer can be treated with a combination of an IL-8 inhibitor and sunitinib.

The protein encoded by IL-8 gene is a member of the CXC chemokine family. The cDNA and amino acid sequences for IL-8 are shown in the attached Sequence Listing identified as SEQ ID NOS. 1 and 2, respectively. IL-8 is secreted by several cell types and is one of the major mediators of the inflammatory response. It functions as a chemoattractant, and is also a potent angiogenic factor. IL-8 and other ten members of the CXC chemokine gene family form a chemokine gene cluster in a region mapped to chromosome 4q.

The present invention includes a method of determining whether a tumor will respond to sunitinib therapy including: providing a biological sample from a tumor; detecting a level of IL-8 expression in the sample; and comparing the IL-8 level in the sample to a suitable control; wherein an elevated IL-8 expression level in the sample as compared to the control indicates the tumor will not respond to sunitinib therapy. With this method, the tumor may be a renal cell tumor; or the control may be the median or average expression level of IL-8 in tumors of the same tissue type that are not resistant to sunitinib therapy.

The present invention also includes a method of determining whether a tumor will respond to sunitinib therapy including: providing a biological sample from a tumor; detecting a level of MMP12 expression in the sample; and comparing the MMP12 level in the sample to a suitable control; wherein an elevated MMP12 expression level in the sample as compared to the control indicates the tumor will not respond to sunitinib therapy. With this method, the tumor may be a renal cell tumor; or the control may be the median or average expression level of MMP12 in tumors of the same tissue type that are not resistant to sunitinib therapy.

Also included is a method for inhibiting the proliferation or causing the death of a tumor cell which is sunitinib-resistant and which expresses IL-8, comprising: contacting a tumor cell which is sunitinib-resistant and which expresses IL-8 with an effective amount of an agent that inhibits IL-8 activity and contacting the tumor cell with an effective amount of sunitinib, whereby proliferation of the tumor cell is inhibited or the tumor cell dies. With this method: (a) the tumor cell may be a renal tumor cell; (b) the tumor cell may be in a mammal and the contacting steps may be carried out by administering the agent to the mammal; or (c) the agent that inhibits IL-8 activity may be selected from an anti-IL-8 antibody, or antigen-binding fragment thereof, an antisense oligonucleotide that inhibits the expression of IL-8, and an RNAi molecule that inhibits the expression of IL-8.

Also included is a method for inhibiting the proliferation or causing the death of a tumor cell which is sunitinib-resistant and which expresses MMP12, comprising: contacting a tumor cell which is sunitinib-resistant and which expresses MMP12 with an effective amount of an agent that inhibits MMP12 activity and contacting the tumor cell with an effective amount of sunitinib, whereby proliferation of the tumor cell is inhibited or the tumor cell dies. With this method: (a) the tumor cell may be a renal tumor cell; (b) the tumor cell may be in a mammal and the contacting steps may be carried out by administering the agent to the mammal; or (c) the agent that inhibits MMP12 activity may be selected from an anti-MMP12 antibody, or antigen-binding fragment thereof, an antisense oligonucleotide that inhibits the expression of MMP12, and an RNAi molecule that inhibits the expression of MMP12.

Another present invention is a composition which includes both an agent that inhibits IL-8 and sunitinib. With this invention, the inhibitor of IL-8 may be an anti-IL-8 antibody, or antigen-binding fragment thereof, an antisense oligonucleotide that inhibits the expression of IL-8, or an RNAi molecule that inhibits the expression of IL-8.

Another present invention is a composition which includes both an agent that inhibits MMP12 and sunitinib. With this invention, the inhibitor of MMP12 may be an anti-MMP12 antibody, or antigen-binding fragment thereof, an antisense oligonucleotide that inhibits the expression of MMP12, or an RNAi molecule that inhibits the expression of MMP12.

The present invention also includes a kit comprising: a first container including an IL-8 inhibitor; a second container including sunitinib; and instructions for using the IL-8 inhibitor and sunitinib to treat cancer. In another embodiment, the cancer may be renal cell carcinoma. Another embodiment of the present invention is a kit comprising: a first container including an MMP12 inhibitor; a second container including sunitinib; and instructions for using the MMP12 inhibitor and sunitinib to treat cancer. In another embodiment, the cancer may be renal cell carcinoma.

The invention also includes methods of treating a sunitinib-resistant cancer in a subject, including; administering to a patient having a sunitinib-resistant cancer a therapeutically effective amount of the above-described compositions thereby treating the sunitinib-resistant cancer. In one embodiment, the cancer is renal cell carcinoma.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown. Drawings are not necessary to scale. Certain features of the invention may be exaggerated in scale or shown in schematic form in the interest of clarity and conciseness.

FIG. 1A shows overexpression of PDGFR-β and VEGFR2 in 174 human clear cell RCC samples (CC) and 15 normal controls (NO) by Affymetrix microarray analysis. Bar plots show the average gene expression level and standard deviation values of each group. P values are also shown. FIG. 1B shows expression of PDGFR and VEGFR in RCC cell lines shown by Western blots. To find out which RTK(s) were SU11248's targets to treat RCC patients, the inventors first examined the expression profile of these RTKs in 174 human clear cell RCC samples by Affymetrix microarray analysis. PDGFR-β and VEGFR-2, but not others, were highly expressed in human ccRCC compared with normal controls (P<0.001, FIG. 1A). To confirm this result, the inventors also examined the expression and activation of the RTKs in RCC cell lines by Western blotting. No significant activation of these RTKs in RCC cells was detected, comparing with the endothelial cell controls. PDGFR-β was expressed by 4 of 12 RCC cell lines, and VEGFR was expressed only by endothelial cell lines (FIG. 1B). FLT3, c-KIT, and RET expression were undetectable in these RCC cell lines.

FIG. 2A shows phosphorylation of PDGFR was inhibited by SU11248 in SN12C and ACHN cells. FIG. 2B shows SU11248 also inhibited PDGF-stimulated activation of ERK and Akt signaling. SU11248 decreased PDGF-stimulted phosphorylation of PDGFR-β at 0.01 μM in both cell lines and completely inhibited the phosphorylation of PDGFR-β from 0.1 μM (FIG. 2A). ERK and Akt were two main downstream effectors in PDGFR signaling pathways. Western blot analysis showed that SU11248 inhibited PDGF-stimulated activation of ERK and Akt at ~0.1 μM, at which concentration SU11248 could significantly inhibit the activation of PDGFR (FIG. 2B).

In order to evaluate if SU11248 could inhibit activation of RTKs and at what level could it inhibit phosphosphorylation, the inventors first serum starved the cells for 24 h, then added SU to pretreat the cells for 2 h, the stimulate cells with ligand for 10 min. Then they performed IP and western blot. As shown here, SU11248 inhibits PDGF-dependent PDGFRβ phosphorylation at 0.01 μM.

In biochemical assays, the inhibition constant (Ki) values for SU11248 against FLK-1 and PDGFRβ are 0.009 μM and 0.008 μM, respectively.

Figure 3:
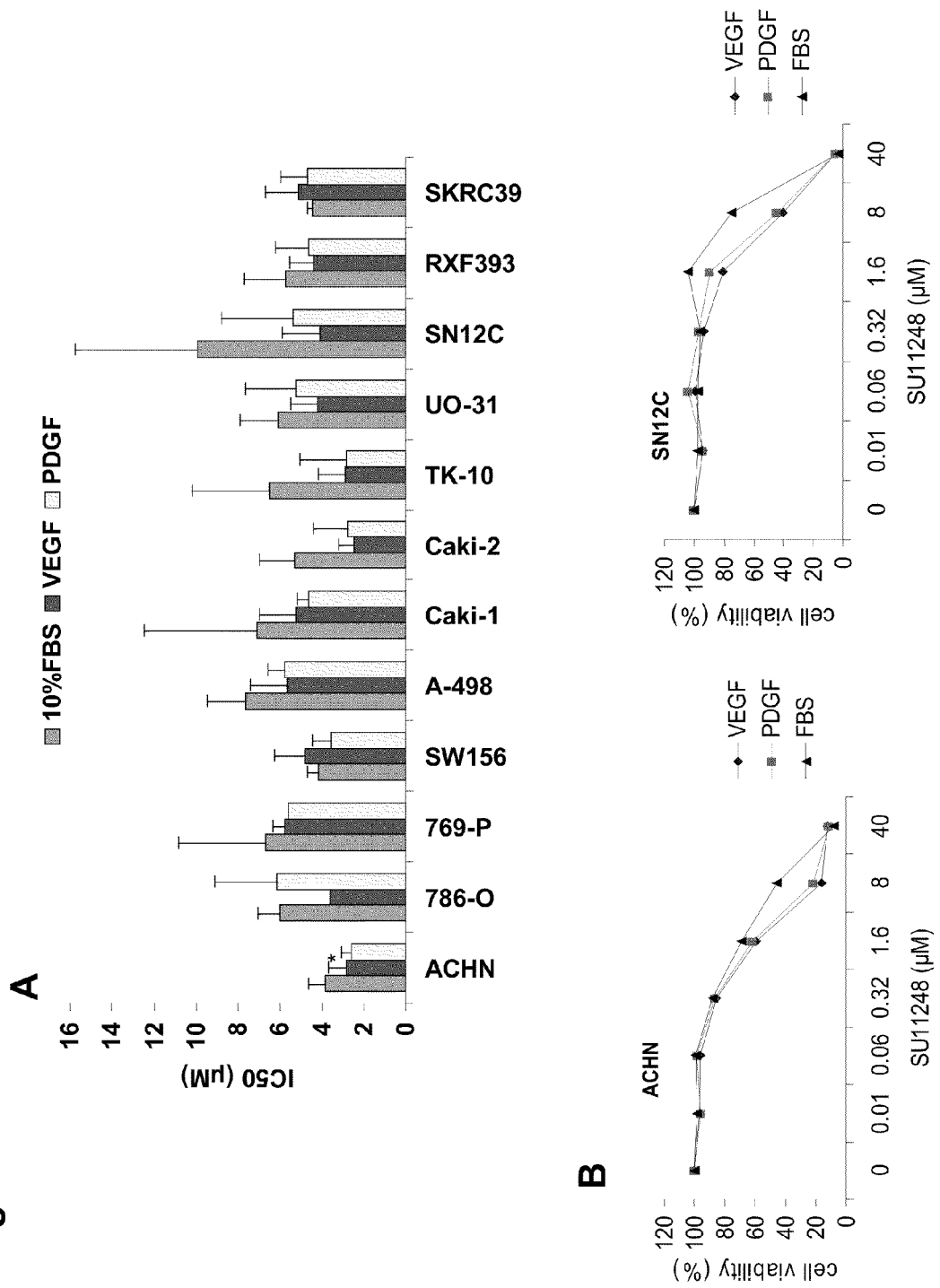
Figure 3:
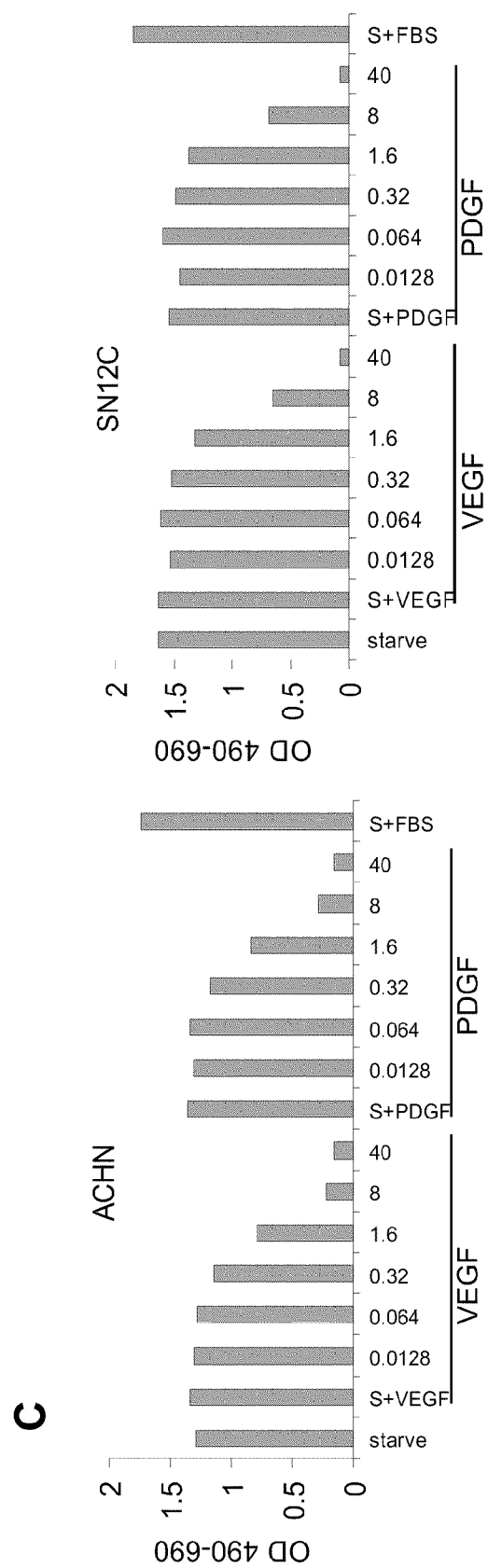

FIGS. 3A-3C show much higher concentrations of SU11248 were required to inhibit proliferation than to suppress PDGFR signaling pathways in RCC cells. FIG. 3A shows IC50 values for SU11248 on RCC cell lines under normal and ligand-dependent conditions. FIG. 3B shows growth curve of SN12C and ACHN cells under normal and ligand-dependent conditions. FIG. 3C shows PDGF alone failed to induce proliferation of RCC cells in vitro. SU11248 inhibited proliferation of RCC cells in a similar pattern under normal culture and ligand-dependent conditions. In both conditions, the IC50s of SU11248 to RCC cell lines were similar (FIG. 3A), at ~4-10 μM, which were much higher than that required to inhibit the phosphorylation of PDGFR-β (0.1 μM). SU11248 showed minimal effect on the proliferation of RCC cells at 0.1 μM, although at which the phosphorylation of PDGFR-β was suppressed (FIG. 3B). This result indicates that inhibition of PDGFR signaling pathway is not sufficient to inhibit the proliferation of RCC cells in vitro. To further explore the role of PDGFR signaling pathways in RCC cells in vitro, the inventors first starved the cells and then activated the PDGFR signaling pathways with PDGF. While FBS could stimulate the proliferation of RCC cells, PDGF alone could not stimulate the proliferation of RCC cells (FIG. 3C).

Figure 4:
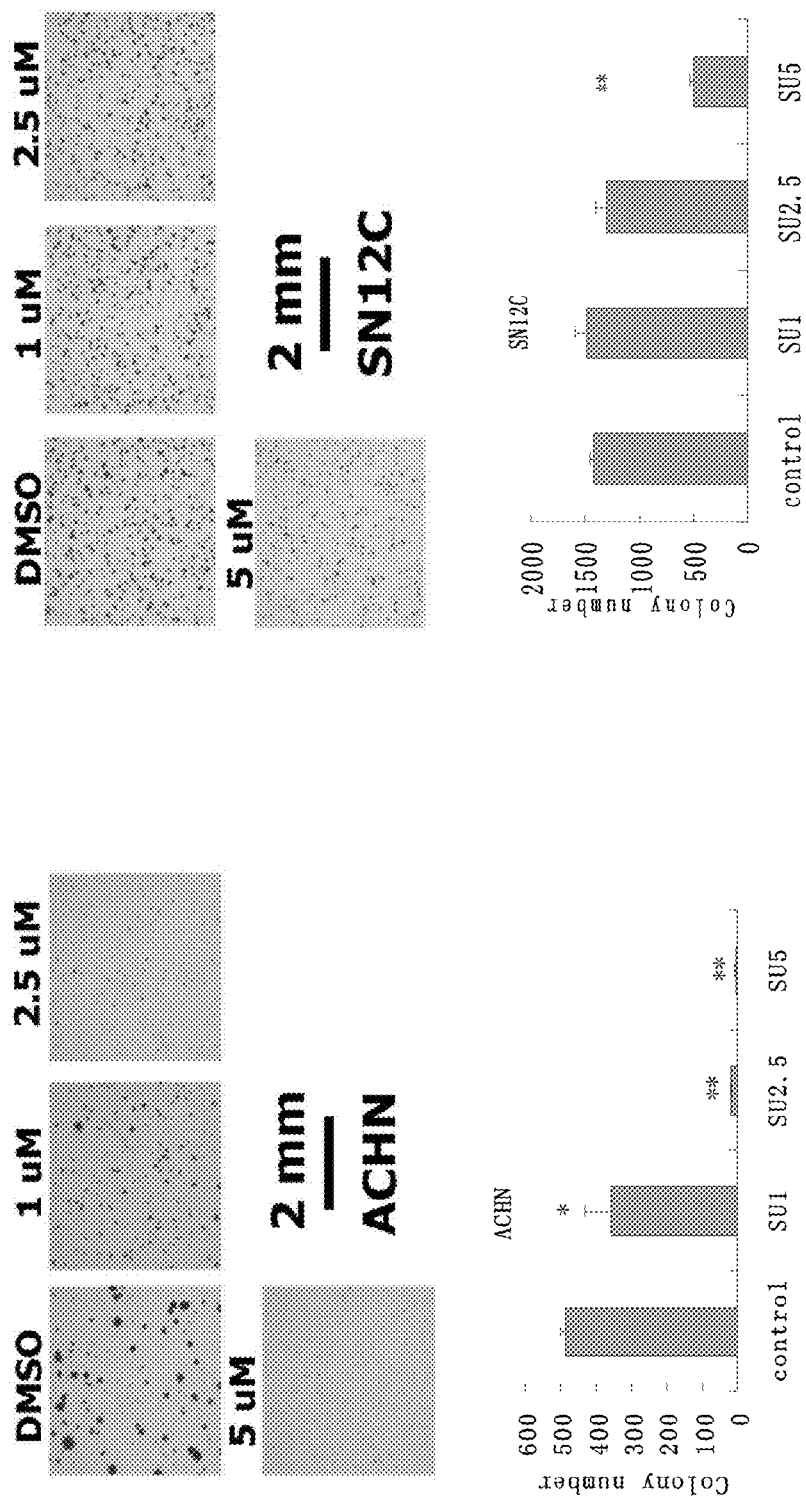

FIG. 4 shows inhibition of colony formation of RCC cells by SU11248 at higher concentrations. Soft agar assay was used to evaluate the effect of SU11248 on the transforming potential of RCC cells. Although SU11248 significantly inhibited the anchorage-independent colony formation of ACHN and SN12C cells at higher concentration (5 μM), it showed minimal effect on ACHN and SN12C cells at 1 μM, at which SU11248 could completely inhibited the activation of PDGFR signaling pathways (FIG. 4). These results are consistent with the proliferation assays. *, P<0.05; **, P<0.01.

The inventors used a three-layer culture system. They plated an agar layer to cover the bottom of plastic plate, then the inventors seeded the cells in the middle agar layer, added drugs in the top medium layer, and the medium was replaced twice per week. The cells were cultured for 14 days. The results for CRL1611 and SN cells are shown here.

Figure 5:
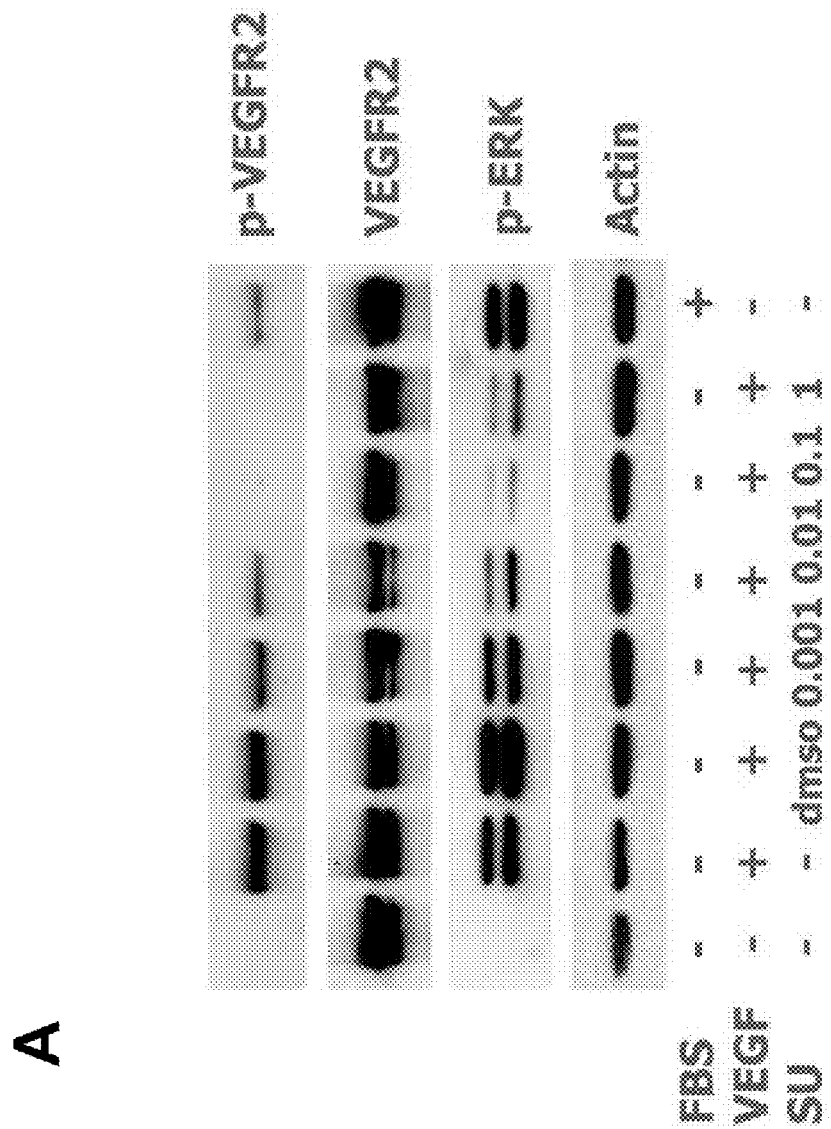
Figure 5:
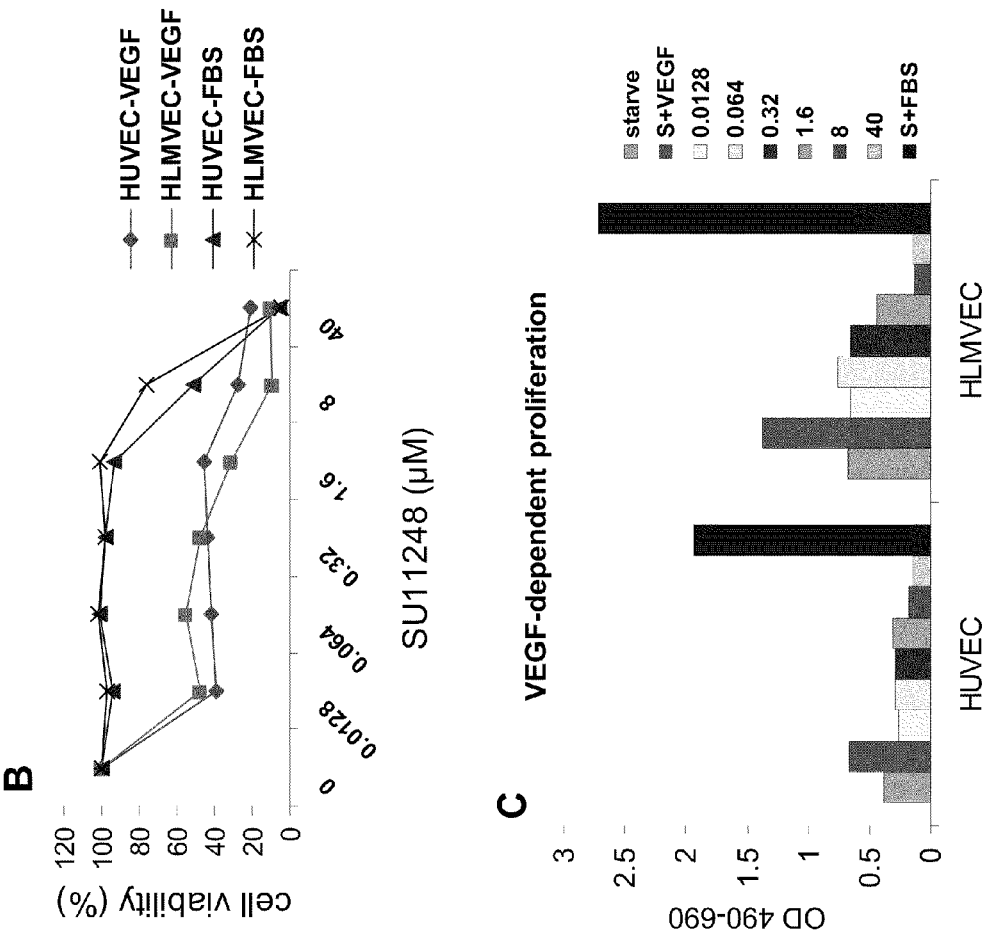

FIGS. 5A-5C show SU11248 inhibited phosphorylation of VEGFR and VEGF-dependent proliferation in endothelial cells. FIG. 5A shows SU11248 inhibited phosphorylation of VEGFR and downstream ERK signaling in HLMVEC cells.

FIG. 5B shows SU11248 inhibited VEGF-dependent proliferation of endothelial cells. FIG. 5C shows both VEGF and FBS could induce proliferation of endothelial cells. The inventors detected the inhibition of phosphorylation of VEGFR in endothelial cell lines by SU11248 using Western blot. SU11248 could inhibit the phosphorylation of VEGFR in HLMVEC cells at similar concentration (0.01-0.01 µM) to that inhibited phosphorylation of PDGFR in RCC cells. Downstream of VEGFR signaling pathways, such as ERK, was also inhibited by SU11248 at this low concentration (FIG. 5A). The direct effect of SU11248 on endothelial cell proliferation in vitro was analyzed by MTS assay. Comparing with RCC tumor cells, SU11248 showed more robust inhibitory effects on the proliferation of HUVEC and HLMVEC cells. IC50s for endothelial cell lines under VEGF-dependent condition were about 0.01 µM, which was identical to the concentration for inhibiting the activation of VEGFR (FIG. 5B). Furthermore, compared with RCC cells, both VEGF and FBS could stimulate the proliferation of endothelial cells, which demonstrates that VEGFR signaling is required for the proliferation of endothelial cells in vitro (FIG. 5C).

Figure 6:
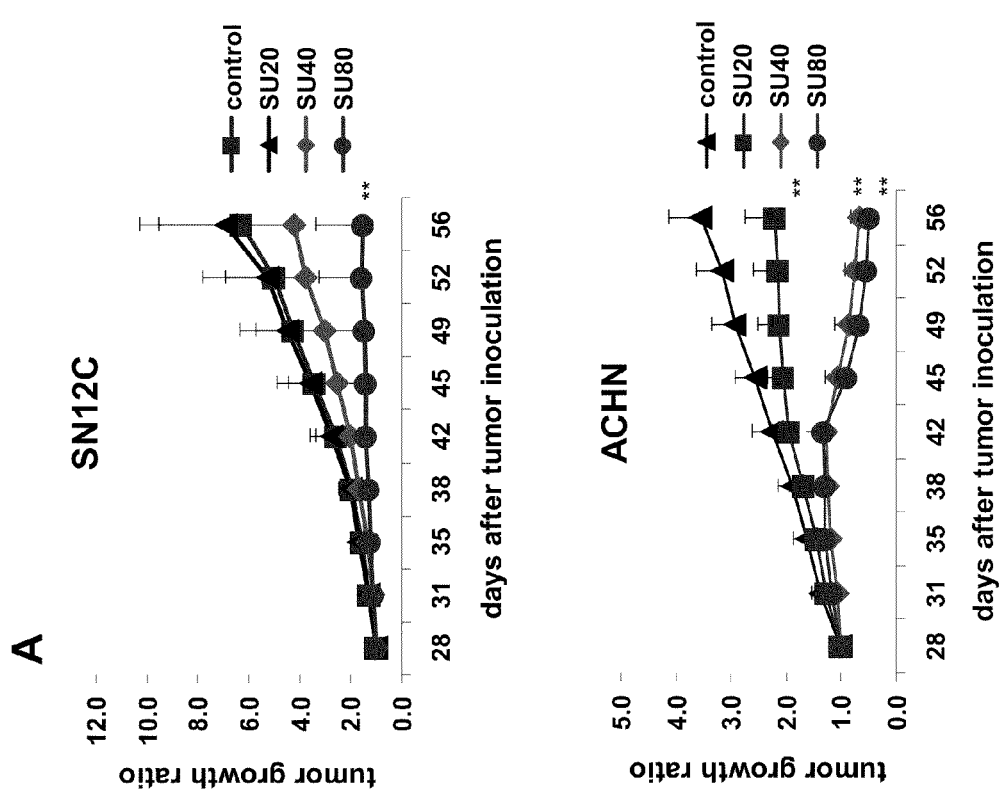
Figure 6:
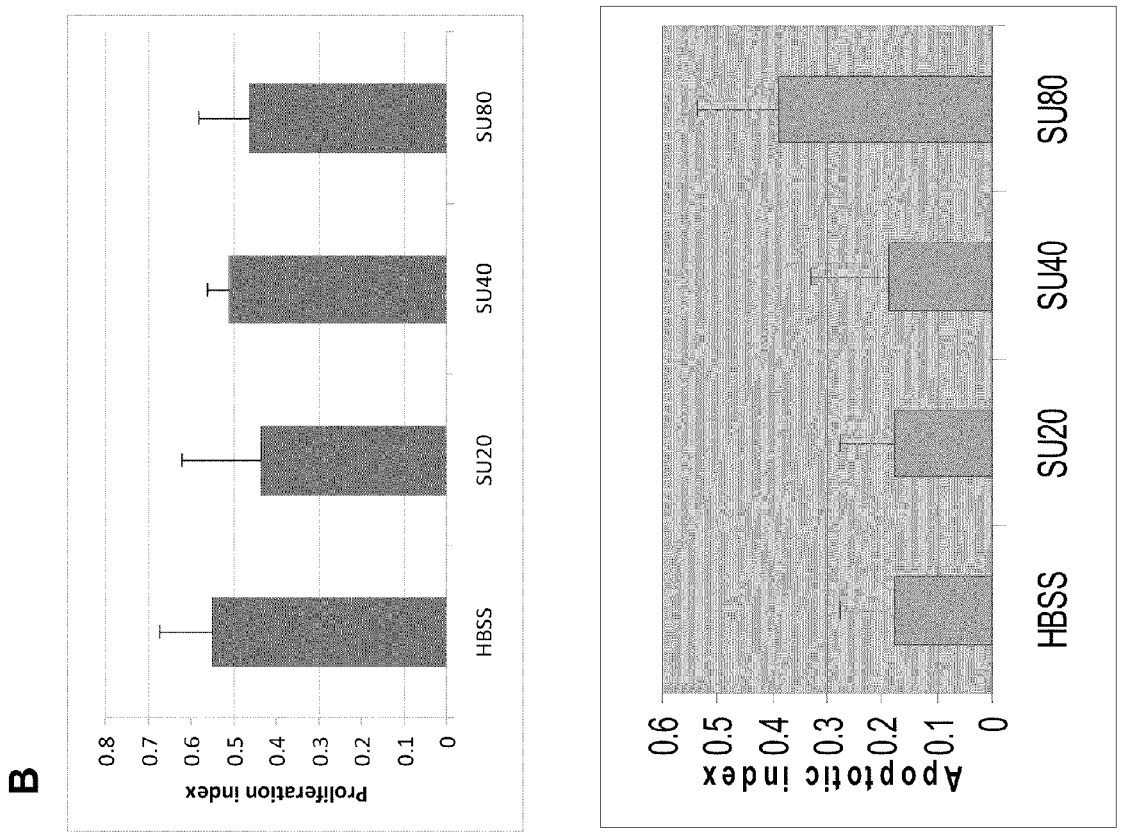

FIGS. 6A-6B show histological analysis of tumor sections treated by SU11248 and vehicle controls. FIG. 6A shows tumor growth was inhibited by SU11248 in RCC xenografts. FIG. 6B shows the effect of SU11248 on proliferation and apoptosis of RCC cells in vivo. SU11248 showed growth inhibition (40 mg/kg) or stasis (80 mg/kg) effect on SN12C xenografts, whereas showed growth inhibition at 20 mg/kg and regression at 40 and 80 mg/kg on ACHN xenografts (FIG. 6A). Extensively necrotic areas in SU11248-treated tumor sections were observed. Therefore, the inventors examined the effect of SU11248 on RCC cell proliferation and apoptosis in vivo by PCNA and TUNEL staining. For SN12C xenografts, the proliferation index (shown as the percentage of PCNA-positive cells) did not change after SU11248 treatment when compared with vehicle controls (FIG. 6B). In SN12C xenografts, no significant increase of apoptotic cells (as shown by apoptosis index) was found after SU11248 treatment (FIG. 6B). This result suggests that SU11248 inhibited the tumor growth in vivo mainly by suppressing the neovascularization. *, P<0.05; **, P<0.01.

Subcutaneous injection of tumor cells, treatment began when tumor volume reached 200 mm 3×daily oral gavage of 3 dosages of SU11248 in a citrate buffer solution. Citrate buffer as vehicle control. Upper panel shows the relative tumor growth ratio after tumor implantation.

Figure 7:
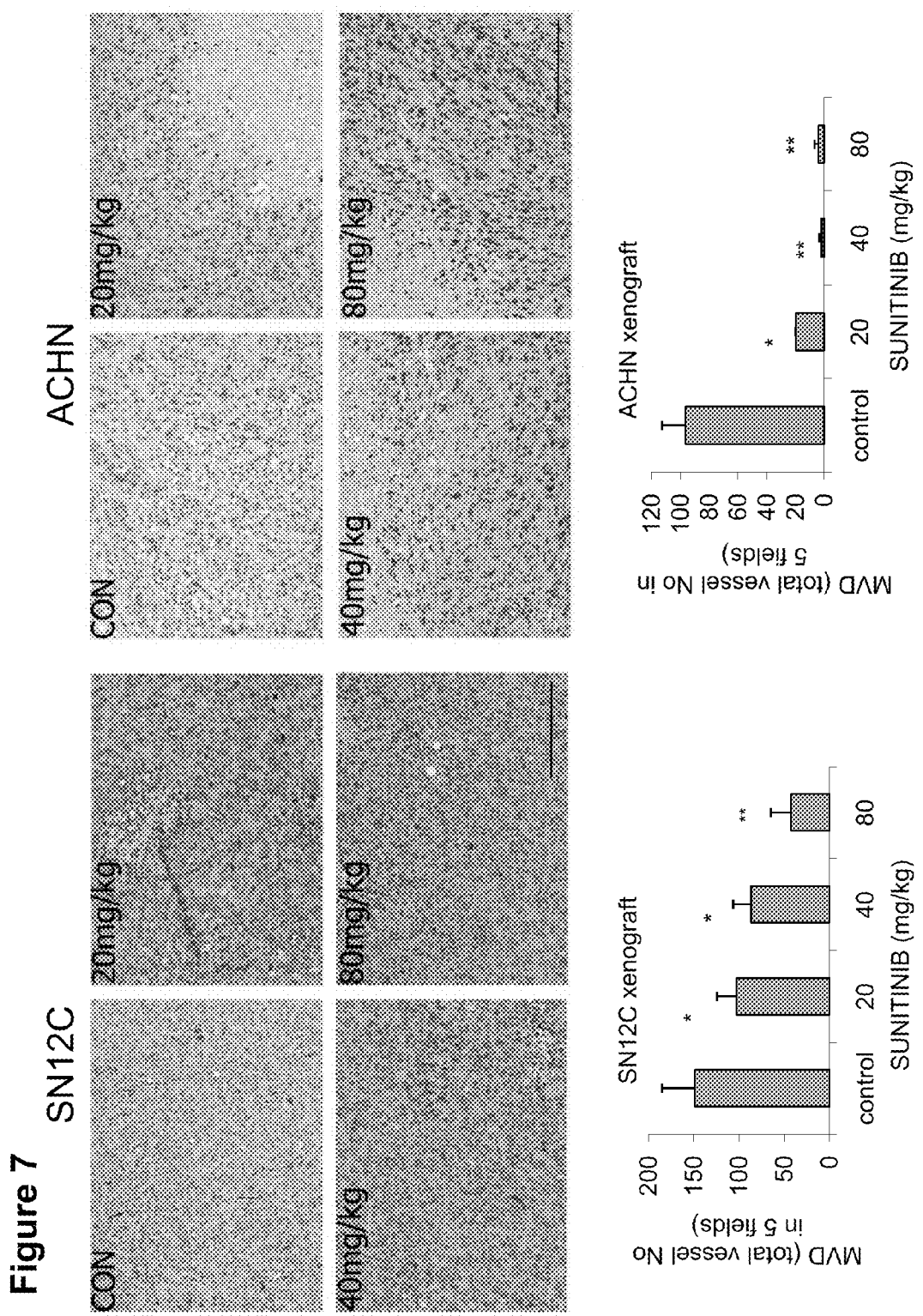

FIG. 7 show SU11248 inhibited tumor angiogenesis in vivo. FIG. 7 shows decreased MVD in SU11248-treated tumor sections. To confirm the effect of SU11248 on tumor endothelium in vivo, the inventors used CD34, a vascular endothelial cell biomarker, to stain the tumor sections and counted the microvessel density (MVD). The MVD was significantly decreased with SU11248 treatment when compared with vehicle controls (P<0.001, FIG. 7). This result suggested that SU11248 inhibited the growth of RCC tumors in vivo by suppressing the tumor angiogenesis.

In clinical, some of the patients showed resistance to SU11248 at first treatment or after the initial response to the drug. So next the inventors used a 3-weeks-on-and-3-weeks-off dosing strategy, which mimicked the clinical process, in xenograft models to induce the SU11248 resistant phenotype.

Figure 8:
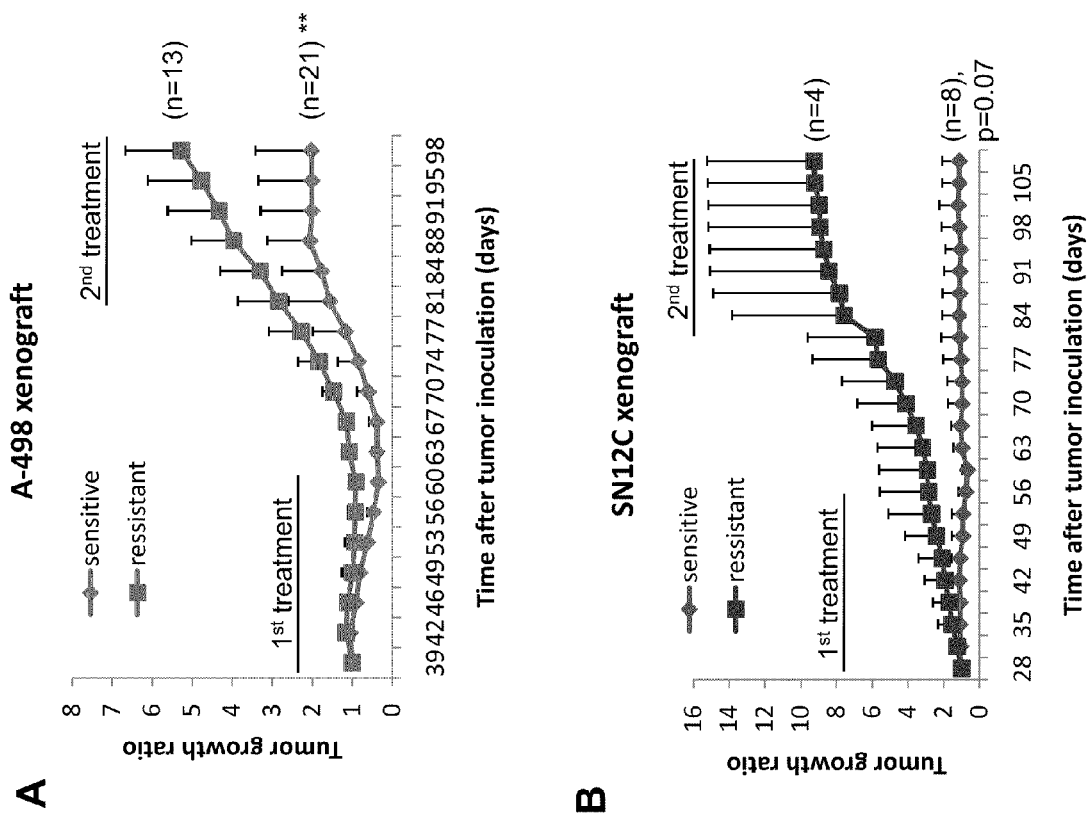
Figure 8:
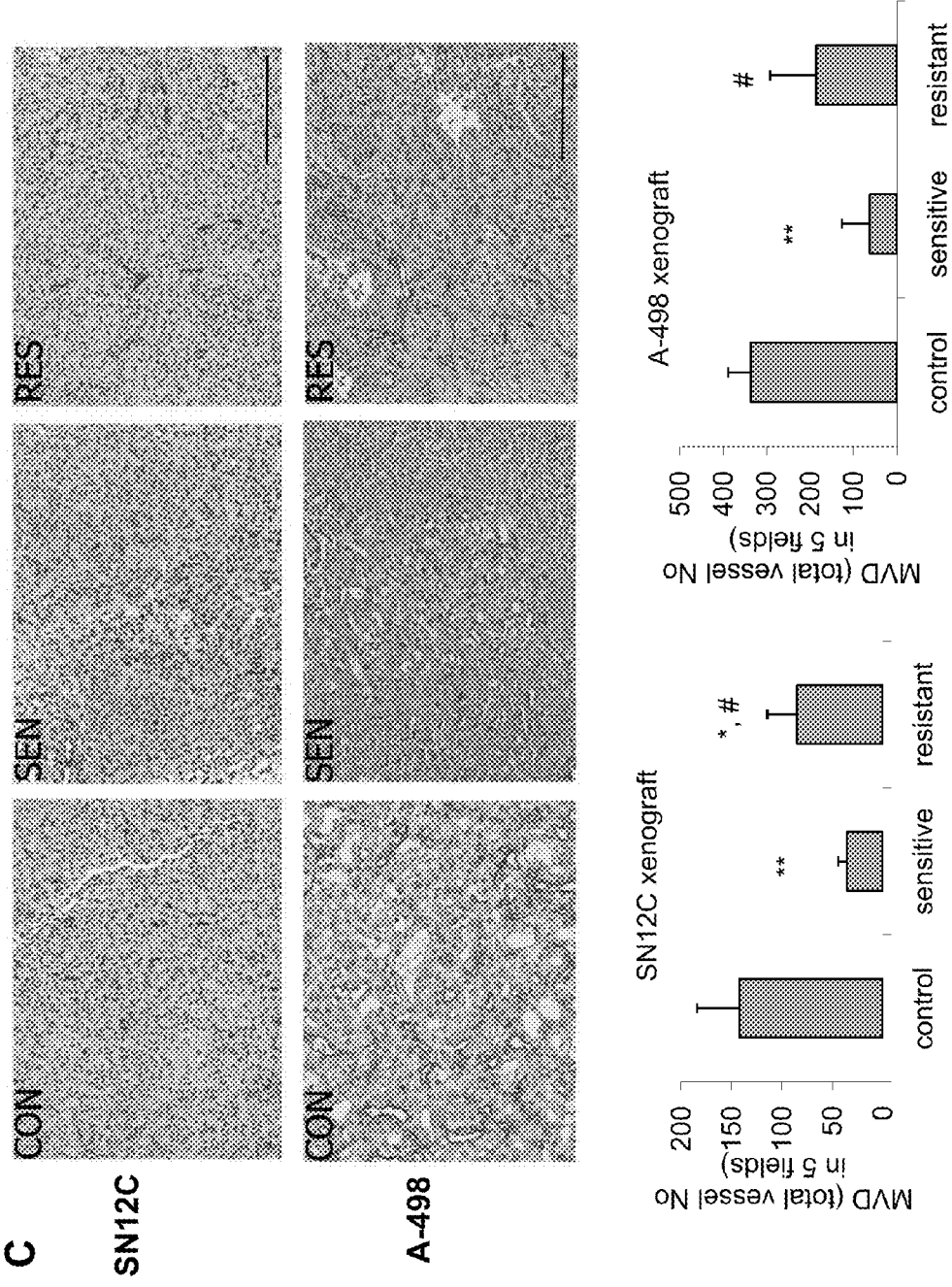
Figure 8:
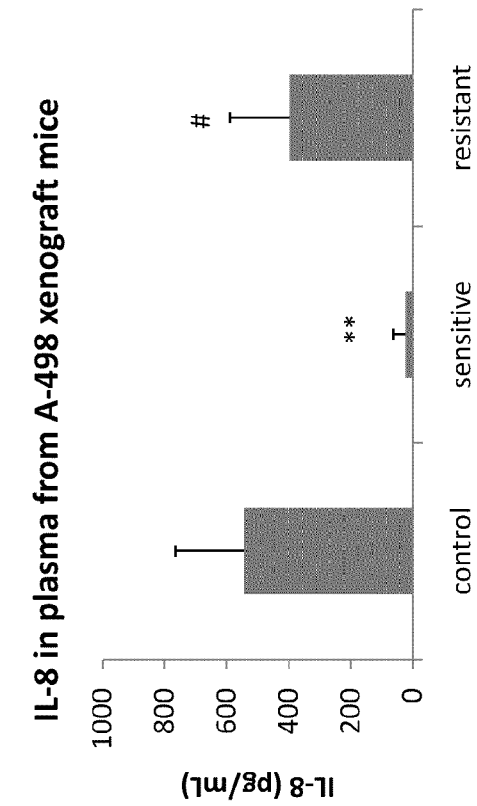
Figure 8:
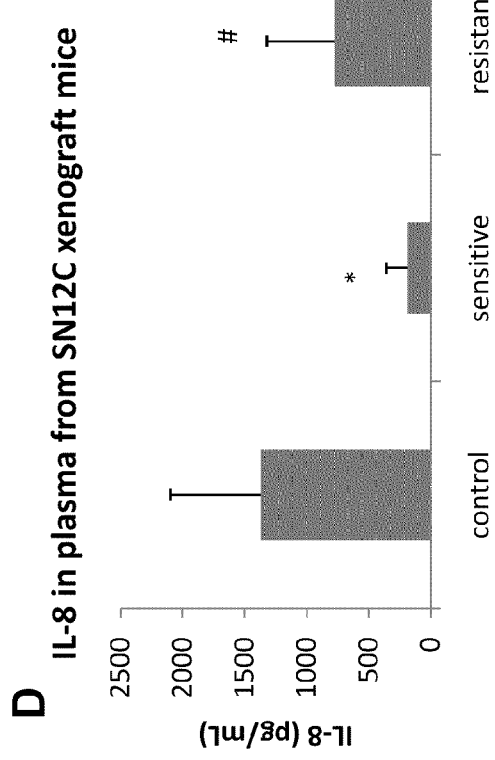

FIG. 8A-8D show escape from anti-angiogenesis and elevated plasma level of IL-8 was found in sunitinib-resistant mice through intermittent dosing. FIG. 8A: sunitinib-resistant mice were identified through growth curves in A-498 xenograft model. Tumor growth ratio was determined by dividing the tumor volume measured at an indicated time by tumor volume at the start of treatment. Tumor growth ratios for each group are presented as mean±standard deviation. A-498 xenografts were treated with 40 mg/kg sunitinib with a 3-weeks-on and 3-weeks-off dosing strategy, which mimicked the clinical regimen given to patients (4-weeks-on and 2-weeks-off) with modification. Thirty eight percent (13/34) of all treated A-498 xenograft mice showed phenotypic resistance to sunitinib with either no response initially or progression at the same doses during $2^{nd}$ round treatment. FIG. 8B: sunitinib-resistant mice were identified through growth curves in SN12C xenograft model. SN12C xenografts were treated with 80 mg/kg sunitinib with the same dosing strategy as A-498 xenografts and 33% (4/12) of all treated SN12C xenograft mice showed phenotypic resistance to sunitinib. FIG. 8C: increased MVD was found in sunitinib-resistant SN12C and A-498 xenograft tumors. The inventors evaluated whether the tumor vasculature was inhibited in the resistant tumors by CD34 staining and quantified MVD using software as indicated in the Examples below. The MVD in the sunitinib-resistant tumors was significantly higher than that in the sensitive tumors. Scale bar, 0.20 mm. FIG. 8D: the reactivation of tumor angiogenesis was accompanied by a significant increase of IL-8 release in the plasma of resistant SN12C and A-498 xenograft mice through ELISA analysis. *, p<0.05 vs. control; **, p<0.01 vs. control; #, p<0.05 vs. sensitive.

FIGS. 9A-9B show escape from anti-angiogenesis and elevated plasma level of IL-8 was found in sunitinib-resistant mice through continuous dosing. FIG. 9A: sunitinib-resistant mice were identified through growth curves in 786-O xenograft model. 786-O xenograft tumors were treated with sunitinib at 40 mg/kg continuously for 34 days (Day 33 to Day 67). Response to sunitinib was presented in 2 phases: sunitinib-responding phase (Day 33 to Day 50), in which the tumor presented stable disease with treatment (tumor growth ratio 1.09); and sunitinib-resistant phase (Day 50 to Day 67), in which the tumor progressed with treatment (tumor growth ratio 1.83). Dashed line separates responding and resistant phase. **, P<0.01. B) The MVD in sunitinib-resistant 786-O xenograft tumors was significantly higher than that found in the sensitive tumors. *, p<0.05. C) Plasma levels of IL-8 were higher in resistant 786-O xenograft bearing mice compared with sensitive mice as analyzed by an ELISA assay. *, p<0.05 vs. control; #, p<0.05 vs. sensitive.

Figure 10:
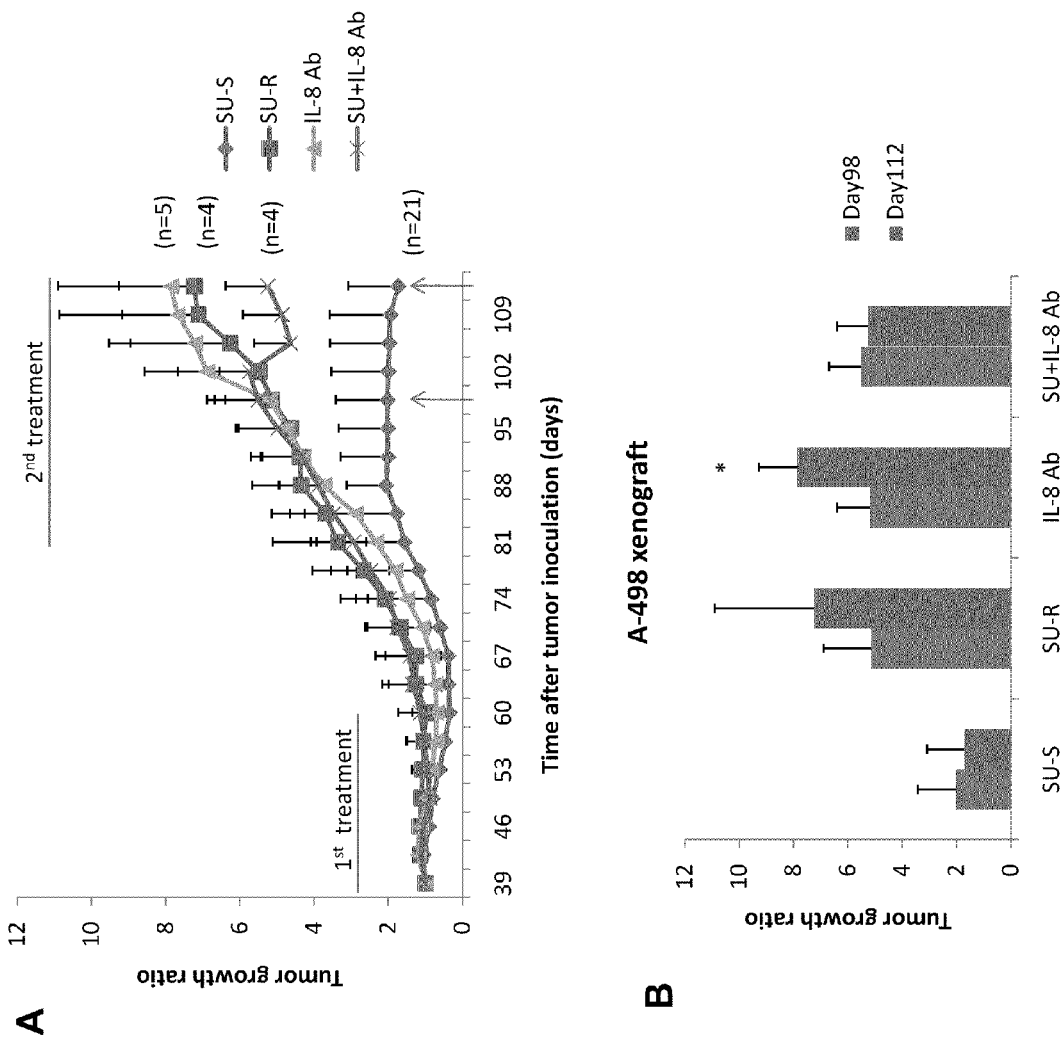
Figure 10:
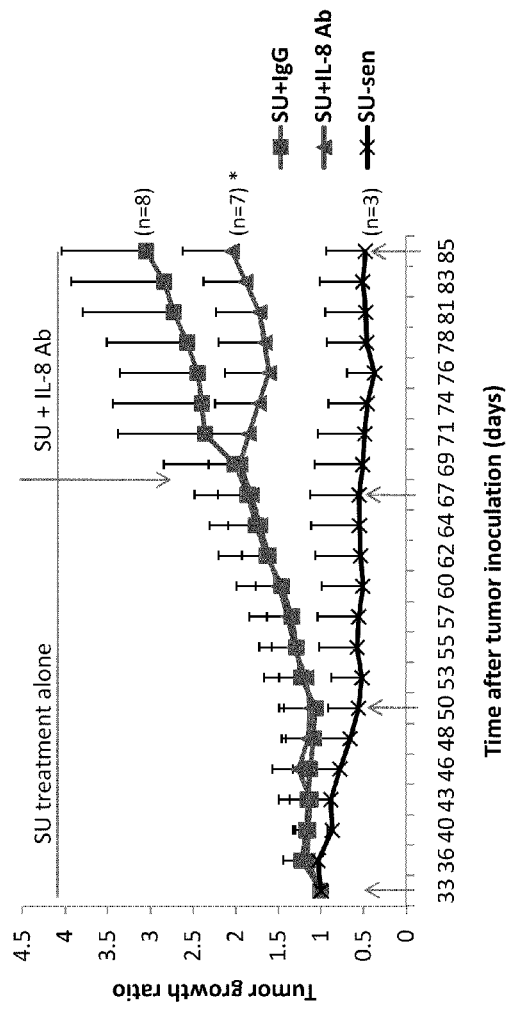
Figure 10:
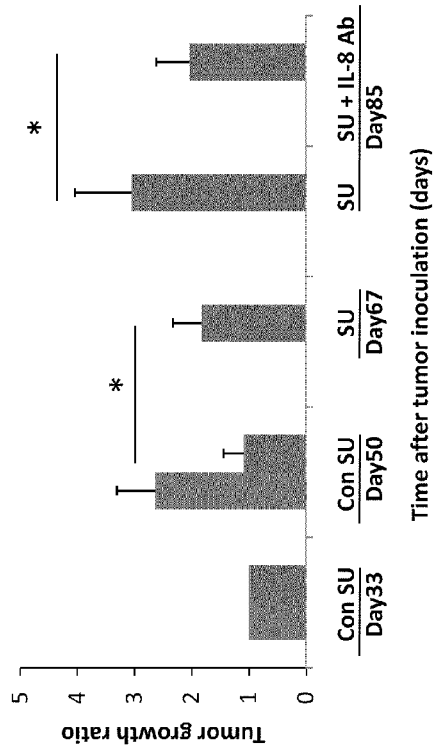
Figure 10:
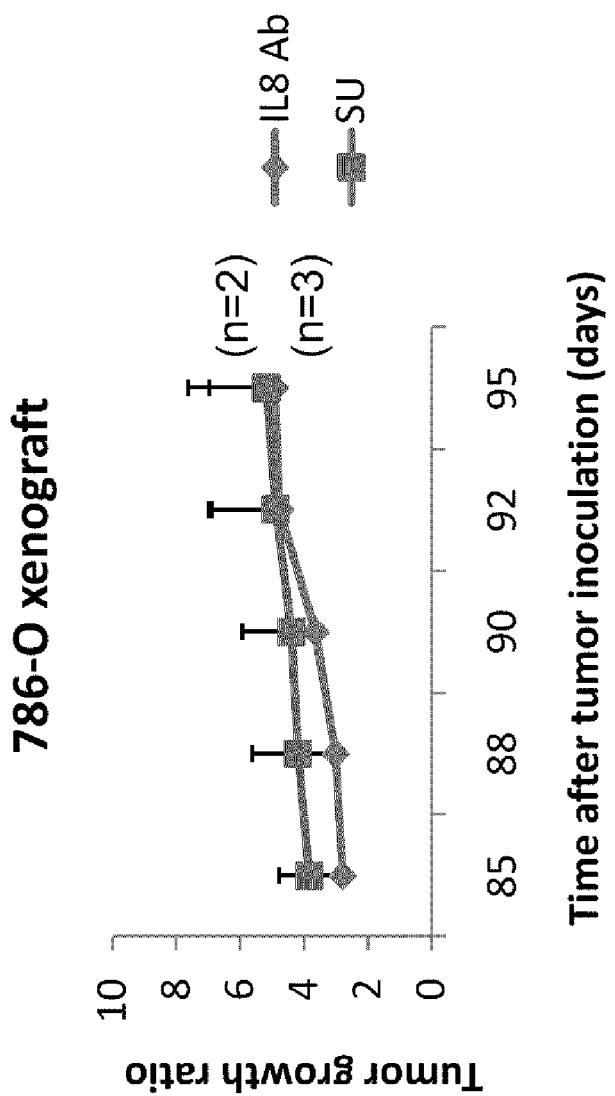

FIGS. 10A-10E show neutralizing of IL-8 activity resensitized RCC xenografts to sunitinib treatment. FIG. 10A shows the reverse of sunitinib resistance in A-498 xenograft model. A-498 xenograft tumors were treated with 40 mg/kg sunitinib intermittently with a 3-week-on and 3-week-off schedule. Sunitinib caused regression of the xenograft tumor. During the 2nd round of SU11248 treatment, some mice stopped responding and regrew and showed phenotypic resistance to sunitinib. Starting from Day 98, SU-resistant mice were randomly divided into 3 groups, one group receiving sunitinib plus IL-8 neutralizing antibody, the second group receiving sunitinib plus control IgG, the third group receiving IL-8 antibody alone. IL-8 neutralizing antibody or control IgG was delivered by ip injection every other day for a total of 7 times. Sunitinib plus IL-8 antibody treatment inhibited tumor growth compared to sunitinib treatment alone (with control IgG) and IL-8 antibody treatment alone. FIG. 10B shows the addition of IL-8 neutralizing antibody inhibited sunitinib resistant tumor growth. Data shown were tumor growth index plotted by different treatment groups. Only the results before (Day 98) and after (Day 112) the addition of IL-8 antibody to sunitinib regimen were shown. Before the addition of IL-8 antibody (Day 98), sunitinib resistant tumor showed phenotypic progression compared with sensitive tumors (SU-S). After the administration of IL-8 antibody (on Day 112), tumor progressed on sunitinib treatment alone (SU-R) since these tumors were resistant to sunitinib; tumor also progressed after switching to IL-8 antibody treatment (SU-R switch IL8 Ab); while the addition of IL-8 antibody to sunitinib regimen (SU-R plus IL8 Ab) inhibited tumor growth compared with Day 98. FIG. 10C shows the reverse of sunitinib resistance in 786-O xenograft model. 786-O xenograft tumors were treated with 40 mg/kg sunitinib continuously. The majority of the mice developed resistance to sunitinib after a period of time treatment. Starting from Day 69, SU-resistant mice were randomly divided into 2 groups, one group receiving SU11248 plus IL-8 neutralizing antibody (SU+IL-8 Ab), and the other group receiving SU11248 plus control IgG (SU+IgG). IL-8 neutralizing antibody or control IgG was delivered by ip injection every other day for a total of 8 times. Sunitinib plus IL-8 antibody treatment inhibited tumor growth compared to sunitinib treatment alone (with control IgG). FIG. 10D shows the addition of IL-8 neutralizing antibody inhibited sunitinib resistant tumor growth. Data shown were tumor growth index plotted with time for sunitinib treatment. The first day (Day 33) of SU11248 treatment was indicated as time 0. SU11248 treatment caused stasis effect on tumor growth after 17 days (Day 50). However, after 34 days (Day 67) of SU11248 treatment, tumors stopped responding and regrew and showed phenotypic resistance to SU11248. Then on the 35th day (Day 68) of sunitinib treatment, IL-8 neutralizing antibody was added to SU11248 regimen and continued for 17 days. On Day 85 (52 days after sunitinib treatment), when all treatment stopped, sunitinib plus IL-8 antibody treatment inhibited tumor growth compared to sunitinib treatment alone (with control IgG). *, $P<0.05$. FIG. 10E shows switching to IL-8 antibody did not inihibit growth of sunitinib resistant 786-O xenograft tumors. After all treatment stopped, some mice from the sunitinib and control IgG treatment group was divided into 2 subgroups, one subgroup receiving sunitinib treatment alone, the other subgroup receiving IL-8 antibody treatment alone. IL-8 antibody treatment alone did not have any effect on growth of sunitinib resistant tumors.

Figure 11:
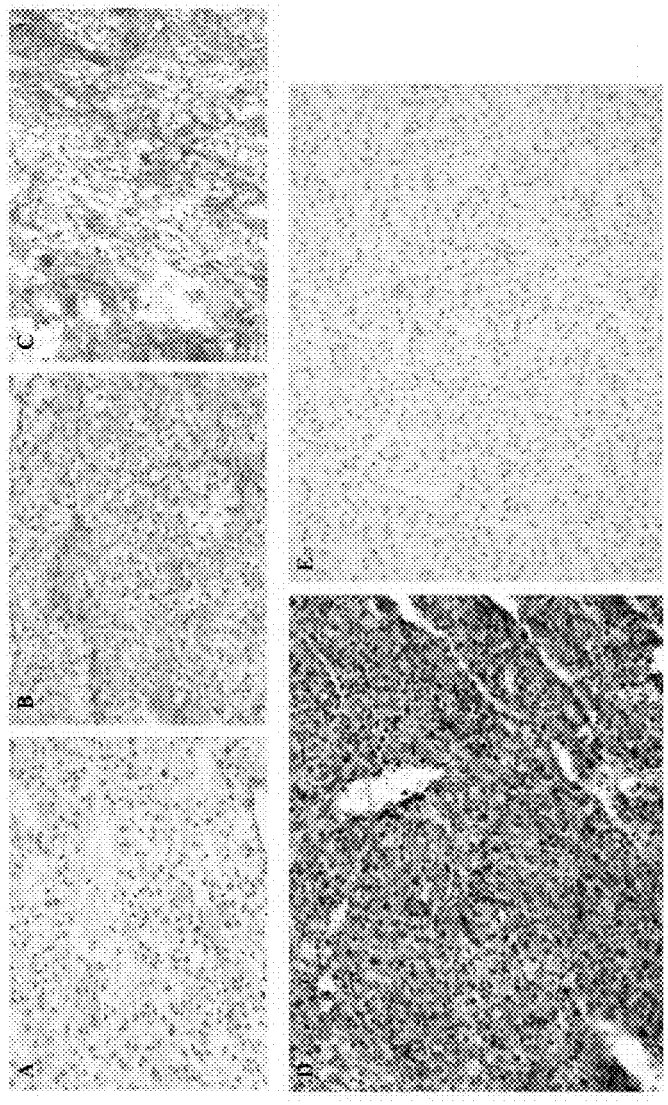

FIGS. 11A-11F show elevated IL-8 expression was found in ccRCC patients who were refractory to sunitinib treatment. Primary tumor sections from ccRCC patients received subsequent sunitinib treatment were stained with IL-8 antibody. Evaluation of IL-8 immunohistochemical staining was shown in (FIGS. 11A-11C). IL-8 positive cells were examined at 40× magnification in peritumoral lymphoid aggregates. Cells with cytoplasmic staining or perinuclear rim were considered positive for IL-8 staining. The cytoplasmic and membranous staining was scored as 0 (negative, FIG. 11A), 1 (weakly positive, FIG. 11B) and 2 (strongly positive, FIG. 11C). In addition, percentage of cells with each staining grade was recorded. A final composite score was calculated as the sum of the percentage of cells multiplied with the staining intensities. FIG. 11D) A ccRCC patient who was refractory to sunitinib treatment had strong IL-8 expression in primary tumor. FIG. 11E: another ccRCC patient who did not progress on sunitinib treatment only had focally weak IL-8 expression in primary tumor. Patient response to sunitinib was evaluated by RECIST criteria. FIG. 11F shows the composite score for IL-8 staining.

Figure 12:
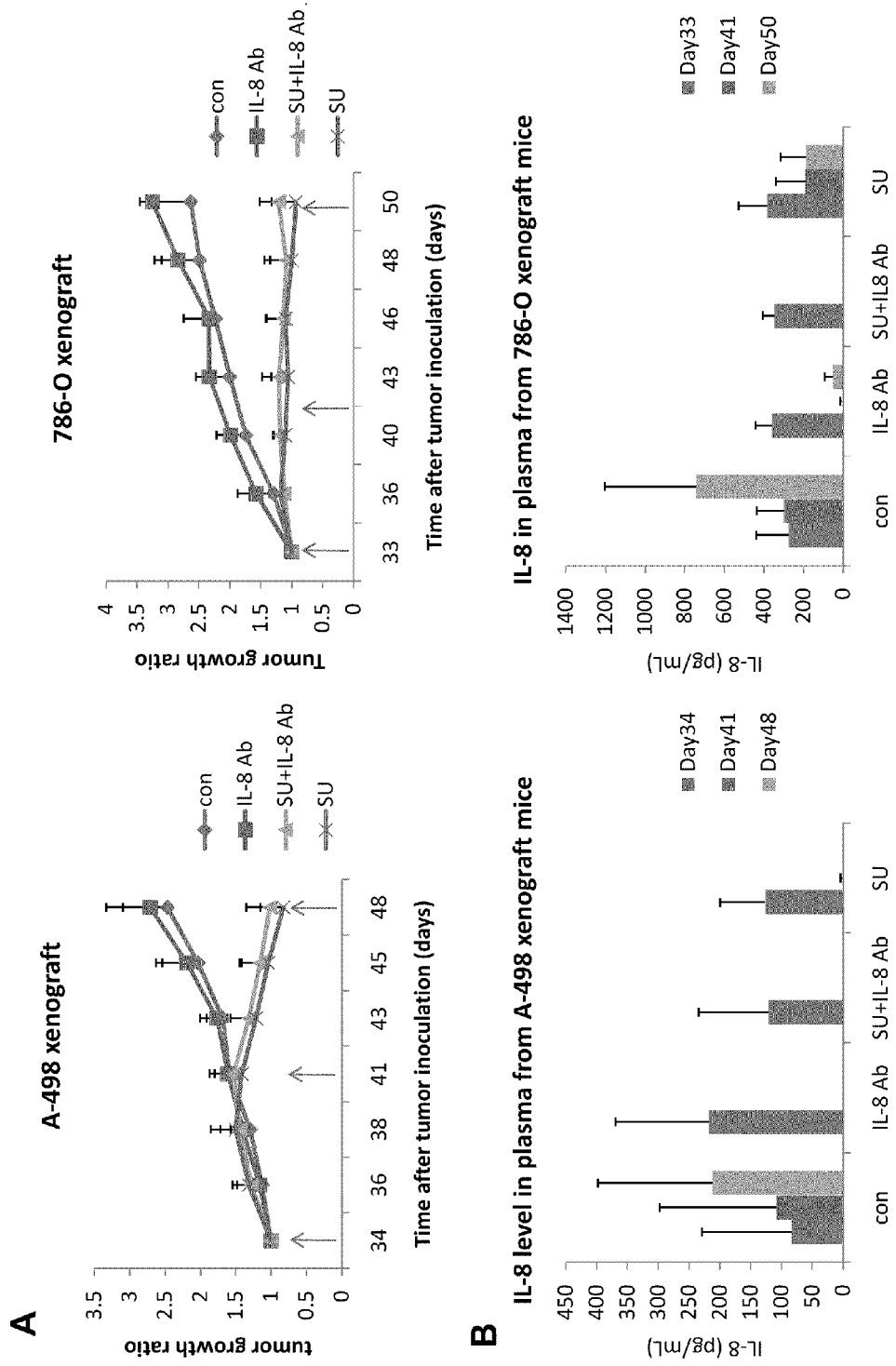

FIGS. 12A and 12B show neutralizing of IL-8 activity alone has no effect on treatment-naïve ccRCC xenograft tumors. A-498 and 786-O tumor bearing mice were randomly divided into 4 groups when the average tumor volume reach 200-300 mm3, receiving control, sunitinib alone, IL-8 neutralizing antibody alone or sunitinib plus IL-8 antibody treatment, respectively. Tumor growth ratio was determined by dividing the tumor volume measured at an indicated time by tumor volume at the start of treatment. Tumor growth indices for each group are presented as mean±standard deviation. N=10 mice for each treatment group. FIG. 12A: IL-8 antibody treatment alone did not have any effect on A-498 and 786-O tumor growth compared to sunitinib alone or the combination treatment. The combination treatment of sunitinib and IL-8 antibody showed similar effect as sunitinib alone. FIG. 12B: neutralizing activity of IL-8 antibody was confirmed by measurement of plasma level of IL-8 from A-498 and 786-O xenograft mice. Reduced plasma levels of IL-8 were detected in both A-498 and 786-O xenograft mice during and after IL-8 antibody treatment (IL-8 Ab groups and IL-8 Ab plus sunitinib groups) by using ELISA method. Arrows in (FIG. 12A) indicates time points when plasma level of IL-8 was detected.

Figure 13:
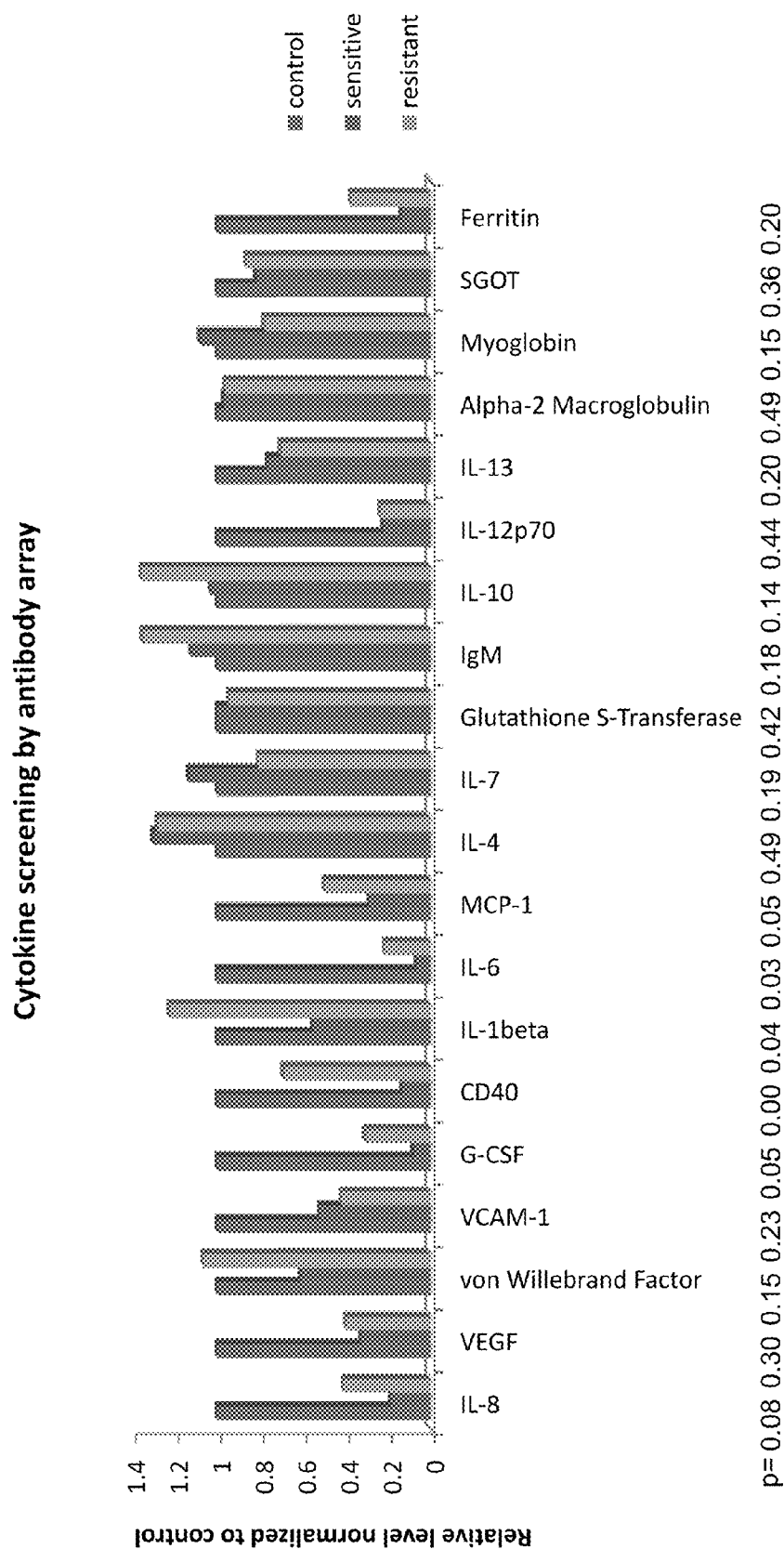

FIG. 13 shows the result of human cytokine screening using antibody arrays. Only detectable factors were shown here. Among the 89 cytokine screened plasma level of IL-8 from sunitinib-resistant tumors, but not VEGF popped up as a pro-angiogenic cytokine compared to sensitive tumors, whereas FGF and EGF were undetectable. Also note the changes of some other pro-inflammatory cytokines, including MCP-1, IL-6, IL-1β, CD40 and G-CSF, indicating a possible increase of infiltration of inflammatory cells in sunitinib resistant tumors. P values between resistant and sensitive samples were shown at the bottom of FIG. 13.

Figure 14:
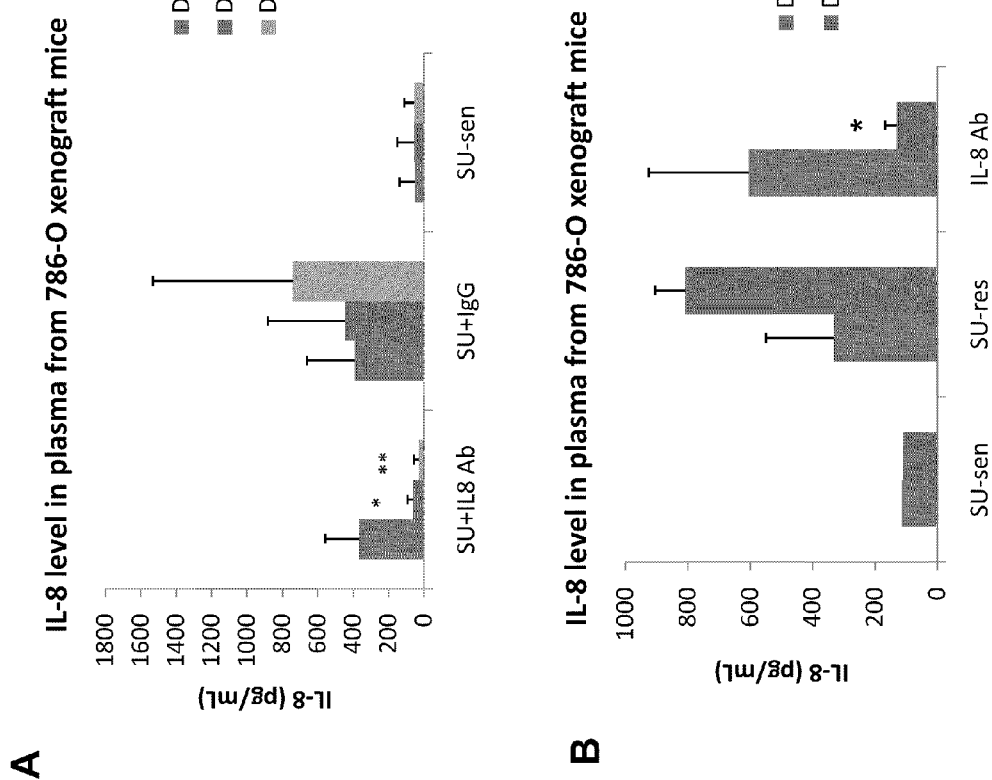

FIGS. 14A and 14B show IL-8 levels in the plasma of 786-O xenograft mice during the course of sunitinib and IL-8 neutralizing antibody treatment. To confirm the neutralizing activity of IL-8 antibody, The inventors also detected plasma level of IL-8 from the 786-O xenograft mice as described in FIGS. 10C and 10D. FIG. 14A: plasma IL-8 levels in 786-O xenograft mice treated with sunitinib or sunitinib plus IL-8 antibody. High plasma level of IL-8 was detected in sunitinib resistant mice (SU+IL8 Ab and SU+IgG) compared to sensitive mice (SU-sen) on Day 68, and IL-8 neutralizing antibody reduced plasma IL-8 level in the combination treatment group, whereas IL-8 plasma level remained high in sunitinib alone treatment group. FIG. 14B: plasma IL-8 level from mice subjected to sunitinib or IL-8 antibody treatment alone. Some sunitinib resistant mice from (FIG. 14A) sunitinib and IgG treated control group were subdivided into 2 groups, one group receiving sunitinib treatment alone (n=2), the other group receiving IL-8 antibody treatment alone (n=3). The neutralizing activity of IL-8 antibody was confirmed by the reduced plasma level of IL-8 compared to sunitinib treatment alone, which maintained high plasma level of IL-8.

DETAILED DESCRIPTION OF THE PREFERRED EMBODIMENTS

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention.

The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples and Sequence Listing included hereafter.

For clarity of disclosure, and not by way of limitation, the detailed description of the invention is divided into the subsections that follow.

The text file filed concurrently with this application, titled "VAN067P393A Sequence Listing.txt" contains material identified as SEQ ID NOS: 1-4 which material is incorporated herein by reference. This text file was created on May 14, 2009, and is 10,042 bytes.

Unless defined otherwise, all technical and scientific terms used herein have the meaning commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. Although any methods, devices and materials similar or equivalent to those described herein can be used in the practice or testing of the invention, the preferred methods, devices and materials are now described.

In this specification and the appended claims, the singular forms "a," "an" and "the" include plural reference unless the context clearly dictates otherwise.

The following abbreviations are used herein: ccRCC, clear cell renal cell carcinoma; RCC, renal cell carcinoma; mTOR, mammalian target of rapamycin; RTKs, receptor tyrosine kinases; VEGFR, vascular endothelial growth factor receptor; PDGFR, platelet-derived growth factor receptor; VHL, von Hippel-Lindau; FBS, fetal bovine serum; LOH, loss of heterozygosity; SDS, sodium dodecyl sulfate; IHC, immunohistochemistry; IF, immunoflourenscence; MVD, microvessel density; IP, immunoprecipitation; RECIST, Response Evaluation Criteria in Solid Tumours.

As used herein, the term "an effective amount" means an amount of the agent, compound or pharmaceutical composition that produces a statistically significant result. For example, with respect to the present invention, an effective amount of an agent, compound or composition means an amount (a) sufficient to inhibit IL-8 or MMP12 activity or (b) that provides the stabilization of or reversal of cancer in a patient. An effective amount can be determined using known techniques, depending upon variables such as the particular type of renal cell carcinoma, the patient, the patient condition, the method of administration, the formulation, and other factors. An effective amount is demonstrated by a statistically significant difference in controlling cell growth, cell proliferation, cell survival, or cell motility as between a treatment group and a control group.

As used herein, "antibody" means an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The term "antibody" includes bivalent or bispecific molecules, diabodies, triabodies, and tetrabodies. Bivalent and bispecific molecules are described in, e.g., Kostelny et al. J Immunol 1992, 148:1547, Pack and Pluckthun Biochemistry 1992, 31:1579, Zhu et al. Protein Sci 1997, 6:781, Hu et al. Cancer Res. 1996, 56:3055, Adams et al. Cancer Res. 1993, 53:4026, and McCartney, et al. Protein Eng. 1995, 8:301. The term "antibody" also includes antigen binding forms of antibodies, including fragments with antigen-binding capability (e.g., Fab', F(ab')2, Fab, Fv and rIgG) and recombinant single chain Fv fragments (scFv). Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Preferably, antibodies employed to practice the present invention bind to a selected target with an affinity (association constant) of greater than or equal to 107 M-1. When an antibody is referred to as specific for a particular antigen (e.g., IL-8 or MMP12), it means that the binding reaction is determinative of the presence of the antigen in a heterogeneous population of proteins and other biologics. Thus, under suitable conditions, the specified antibodies bind to a particular protein sequences at least two times the background and more typically more than 10 to 100 times the background.

The term "biological sample" means any fluid or other material derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term is a organ or tissue extract and a culture fluid in which any cells or tissue preparation from the subject has been incubated.

The term "cell" is used in its usual biological sense, and does not refer to an entire multicellular organism. The cell can, for example, be in vitro, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

"Patient" refers to a mammal, preferably a human, in need of treatment for a condition, disorder or disease.

"Subject" or "patient" refers to a mammal, preferably a human, in need of treatment for a condition, disorder or disease.

By "treatment" or "treating" it will be understood that this refers to any administration of a small molecule (e.g., sunitinib), a polypeptide, oligonucleotide, agent, or combination thereof, intended to alleviate the severity of a disease being treated, to provide relief from the symptoms of the disease or to prevent or slow down the development of the disease in an individual with a disease condition or at risk of developing the disease condition.

By "therapeutically effective amount" is meant a dose that produces the therapeutic effect for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

The term "tumor cell" refers to a cancerous, pre-cancerous or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. A "tumor" includes at least one tumor cell.

Clear cell subtype accounts for 85% of all RCC. The Von Hipple Lindau (VHL) gene is frequently mutated in 75% of clear cell RCC patients. Since the VHL protein is critically involved in ubiquitin-mediated degradation of HIF-1α, mutations in the VHL gene result in HIF-1α accumulation and VEGF and PDGF overexpression. RCC cells expressed high level of VEGF, which leads to highly vascularized tumors. The treatment for metastatic RCC was highlighted by the approval of SU11248, which showed ~40% response rate in clinical trials. It is postulated that PDGFR and/or VEGFR are the targets of SU11248 in RCC cells. The inventors showed that SU11248 targeted PDGFR and VEGFR signaling pathways in RCC cells and endothelial cells, respectively, but both mechanisms contributed to the same anti-angiogenesis effect on RCC tumor growth in vivo.

SU11248 inhibited phosphorylation of PDGFR in RCC cells at 0.01-0.1 μM, but inhibited proliferation of RCC cells with IC50 at 2-6 μM (ligand-dependent condition, and 4-10 μM in complete medium). No difference was observed when comparing the IC50 values under different conditions. The fact that PDGF and VEGF failed to stimulate proliferation of RCC cells further demonstrated that PDGFR and VEGFR signaling are not required for RCC cells proliferation.

Inhibition of ERK signaling alone did not have much effect on proliferation of RCC cells, which demonstrated the existence of other proliferation signaling in RCC cells. This finding is also consistent with the inventors previous study in which it was shown that inhibition of MKK/MAPK signaling with MKK inhibitor LeTx only modestly affected RCC cells proliferation 19. In contrast, inhibition of ERK signaling in endothelial cells dramatically suppressed proliferation. This finding also indicated that activation of redundant signaling pathway exists in RCC patients. This may be why no patients got complete response with single targeted therapeutics.

In vivo, a similar result was observed. Proliferation of SN12C and ACHN cells (as shown by PCNA staining) was weakly inhibited by SU11248 treatment without induction of apoptosis (as shown by TUNEL staining). Despite the weak anti-proliferation effect of SU11248 on RCC cells, profound tumor growth inhibition was observed after SU11248 treatment in RCC xenograft models. Extensive necrosis was also observed in the center of tumors. Since weak or modest effects of SU11248 on tumor cell proliferation and apoptosis were observed, the anti-tumor effect in vivo is most likely caused by the anti-angiogenic effect. The extensive tumor necrosis may be a result of the interruption of tumor vasculature.

Preclinical and clinical studies have revealed that a plasma concentration of 50-100 ng/ml (0.1-0.25 μM) is the effective and achievable dose, which could be achieved by 40-80 mg/kg SU11248 daily oral gavage in mice in the present work 12, 20-22. Using this dosing strategy, tumor growth was significantly inhibited by suppression of tumor neovascularization. The fact that SU11248 inhibited proliferation of endothelial cells through suppression of VEGFR signaling suggests that it may act directly on endothelial cells in vivo.

Other studies have also shown SU11248 attenuated the migration and capillary-like tubule formation ability of endothelial cells 23, 24.

Through an unknown mechanism, almost all patients will become resistant after treatment with SU11248 for about one year. The inventors' studies showed that SU11248 exhibited its effect mainly through disruption of tumor vasculature, which lead them to hypothesize that the resistance was due to the alteration of this anti-angiogenic effect. Thus, the inventors analyzed the microvessel density (MVD) of sunitinib-resistant, sunitinib-sensitive and control tumor sections and found increased MVD in resistant tumors compared to sensitive. Angiogenesis is regulated by both pro-angiogenic and angiostatic factors. The inventors collected plasma samples from sunitinib-resistant, sunitinib-sensitive, and control mice and performed cytokine screening. IL-8, which is a potent pro-angiogenic cytokine, was found to be elevated in the plasma from sunitinib-resistant mice. IL-8 is a potent pro-angiogenic chemokine that binds to specific G protein-coupled CXC chemokine receptors (CXCR2 and CXCR1) and promotes angiogenesis through the enhancement of endothelial cell proliferation, chemotaxis, survival, and protease activation. The expression of IL-8 gene in SU11248-resistant tumors was also found elevated compared to sensitive. Thus, cancer cell may bypass the angiogenic inhibition by upregulation of certain pro-angiogenic factors, which may account for the resistance and be targeted for subsequent treatment. Furthermore, this result was validated in human samples. Higher IL-8 gene expression level in five SU11248-non-responded tumor samples compared to two responded tumors. Since the tumor samples were taken prior to SU11248 treatment, this result indicates that IL-8 level may be used to predict response to SU11248.

SU11248 showed a profound effect on angiogenesis in RCC by inhibition of the proliferation of tumor-associated endothelial cells by targeting VEGFR signaling pathways. On the other hand, the anti-angiogenesis-escape in sunitinib-resistant RCC tumors by inducing the release of some pro-angiogenic factors, such as IL-8, indicates that other anti-angiogenic methods by targeting other signaling pathways are still needed, especially for sunitinib-resistant patients. As discussed below, one such method would be treating sunitinib-resistant RCC with an IL-8 inhibitor.

A sunitinib-resistant RCC tumor generally is less affected or is unaffected by the administration on sunitinib in that the cells of the RCC tumor will grow, proliferate, and/or metastasize despite the presence of the sunitinib. The present invention can be used in a method for treating cancer, including RCC-related conditions or diseases. Such treatment will be directed to treating a patient in need of controlling cell growth, cell proliferation, cell survival, or cell motility. In addition to renal cell carcinoma, sunitinib also can be administered to treat other cancers, such as, GIST (gastrointestinal stromal tumor), breast cancer, SCLC (small cell lung cancer), colon cancer, AML (acute myeloid leukemia), CML (chronic myelogenous monocytic leukemia), glioma, and melanoma. With these cancers, the tumor may become sunitinib-resistant. As with renal cell carcinoma, despite the administration of sunitinib to the patient, a sunitinib-resistant tumor generally is less affected or is unaffected by the administration on sunitinib in that the cells of the tumor will grow, proliferate, and/or metastasize. Thus, it is anticipated that the inventions disclosed herein will be effective in any sunitinib-resistant cancer in which IL-8 or MMP12 is upregulated as compared to non-resistant tumors of the same type.

The reversal of sunitinib resistance by a neutralizing IL-8 antibody further demonstrated that IL-8 played an important role in the acquired resistance to sunitinib. Both cytokine screening and gene expression profiling by microarray also showed that some other members of the chemokine family were simultaneously upregulated in the sunitinib-resistant tumors. Here, the inventors showed in ccRCC that when VEGF/VEGFR signaling is inhibited in vivo, IL-8 may be adopted as a compensatory signaling to circumvent sunitinib induced blockage of angigenesis.

Further, the inventors demonstrate for the first time that in the context of ccRCC the escape from the first line anti-angiogenic therapy (sunitinib) is related to the upregulation of IL-8. Importantly, through antibody array analysis the elevation of pro-angiogenic factors in the plasma of sunitinib-resistant tumor was only observed for IL-8, but not for VEGF and bFGF, indicating the major role of IL-8 in this reacquisition of tumor angiogenesis. Ebos et al. reported that multiple circulating growth factors, cytokines, and chemokines were elevated after sunitinib treatment in a dose-dependent and tumor-independent fashion in non-tumor bearing mice, including VEGF, P1GF, G-CSF, SDF-1α, and SCF. This study done in non-tumor-bearing mice also support the inventors finding that the IL-8 level change observed with sunitinib treatment may be tumor-dependent.

To validate this result in human ccRCC, the inventors also examined IL-8 expression in ccRCC patients who were given sunitinib treatment after nephrectomy. Although the inventors have limited samples, consistent with the inventors' xenograft data, stronger IL-8 immunohistochemical staining was found in tumor samples from patients who were refractory to sunitinib treatment. More importantly, as the tumor samples were removed prior to sunitinib treatment, this result indicates that the level of IL-8 may be used to predict response to sunitinib in a larger patient population.

Since IL-8 signaling is activated in response to sunitinib inhibition of angiogenesis (VEGF/VEGFR signaling), the inventors examined whether targeting of IL-8 would have therapeutic effect on ccRCC in the first place. The inventors examined the consequence of neutralizing IL-8 activity in treatment-naive tumors, and found that inhibition of IL-8 alone does not have any efficacy at all.

In summary, the inventors demonstrated that IL-8 mediated compensatory pro-antiogenic signaling accounts for the reangiogenesis of ccRCC tumor phenotypically resistant to sunitinib treatment in an animal model. Therefore, with the present invention, IL-8 can be inhibited in sunitinib resistant ccRCC (or other sunitinib-resistant cancers) to reestablish sunitinib sensitivity and extend the efficacy of treatment with this agent, in addition to its role as a biomarker for sunitinib response.

The present invention includes a method of treating a patient with a sunitinib-resistant tumor by administering to the patient an effective amount of a compound that targets and/or inhibits the expression or activity of IL-8 or MMP12 or their downstream targets in a tumor cell, and also administering to the patient a therapeutically effective amount of sunitinib. In one embodiment, the tumor is an RCC tumor. With the novel combination of such compound and sunitinib, it is expected that the tumor will respond to the sunitinib therapy in that cell growth, cell proliferation, cell survival, and/or cell motility of the tumor will be controlled or reduced.

One example of an IL-8 inhibitor is an antibody specific to IL-8 or MMP12. An antibody specific to IL-8 is an antagonist that competitively inhibits binding of the IL-8 to its receptor and thereby inhibits activation of the signaling pathway that is otherwise (absent the IL-8 antibody) activated by IL-8.

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss,-Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)). Techniques for the production of single chain antibodies or recombinant antibodies (U.S. Pat. No. 4,946,778, U.S. Pat. No. 4,816,567) can be adapted to produce antibodies to polypeptides of this invention, i.e., an anti-IL-8 antibody or an anti-MMP12 antibody. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Another example of the agents that inhibit IL-8 or MMP12 is a nucleic acid molecule that inhibits IL-8 or MMP12 gene expression. Examples of such nucleic acid molecules include antisense oligonucleotides, RNA interference (RNAi) molecules such as siRNA (small interfering RNA) molecules, and shRNA (short hairpin RNA) molecules. Given the cDNA sequences of IL-8 and MMP12 are known (SEQ ID NO: 1 and 3 respectively), it is well within the capability of a skilled artisan to develop such nucleic acid molecules. Both non-viral and viral vector delivery systems can be used to deliver the nucleic acid molecules to a tumor cell. For a review of gene therapy procedures, see Anderson, Science 1992, 256: 808-813; Nabel & Felgner, TIBTECH 1993, 11:211-217; Mitani & Caskey, TIBTECH 1993, 11:162-166; Dillon, TIBTECH 1993, 11:167-175; Miller, Nature 1992, 357:455-460; Van Brunt, Biotechnology 1988, 6:1149-1154; Vigne, Restorative Neurology and Neuroscience 1995, 8:35-36; Kremer & Perricaudet, British Medical Bulletin 1995, 51:31-44; Haddada et al., in Current Topics in Microbiology and Immunology Doerfler and Bohm (eds) (1995); and Yu et al., Gene Therapy 1994, 1:13-26.

In some embodiments, small interfering RNAs are administered. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, Nature 2001, 411:428-29; Elbahir et al., Nature 2001, 411:494-98; and Fire et al., Nature 1998, 391:806-11, where methods of making interfering RNA also are discussed. The siRNA inhibitors are less than 100 base pairs, typically 30 bps or shorter, and are made by approaches known in the art. Exemplary siRNAs according to the invention can have up to 29 bps, 25 bps, 22 bps, 21 bps, 20 bps, 15 bps, 10 bps, 5 bps or any integer thereabout or therebetween.

Methods of non-viral delivery of nucleic acid molecules include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Delivery can be to cells (ex vivo administration) or target tissues (in vivo administration). The preparation of lipid: nucleic acid complexes, including targeted liposomes such as immunolipid complexes, is well known to one of ordinary skill in the art (see e.g., Crystal, Science 1995, 270:404-410; Blaese et al., Cancer Gene Ther. 1995, 2:291-297; Behr et al., Bioconjugate Chem. 1994, 5:382-389; Remy et al., Bioconjugate Chem. 1994, 5:647-654; Gao et al., Gene Therapy 1995, 2:710-722; Ahmad et al., Cancer Res. 1992, 52:4817-4820; and U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of the nucleic acid molecules are known in the art. Conventional viral based systems for the delivery of such nucleic acid molecules include retroviral, lentivirus, adenoviral, adeno-associated and herpes simplex virus vectors for gene transfer.

It may be desirable that the gene therapy vector be delivered with a high degree of specificity to a particular tissue type, such as renal tumor. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., Proc Natl Acad Sci USA 1995, 92:9747-9751, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient (include humans and other mammals such as mice and rats), typically by systemic administration (e.g., intravenous, intraperitoneal, intramuscular, subdermal, or intracranial infusion) or topical application, as described below.

Vectors (e.g., retroviruses, adenoviruses, liposomes, etc.) containing therapeutic nucleic acids can also be administered directly to the patient for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Compounds that inhibit IL-8 or MMP12 expression or activity could be identified in a cell expressing IL-8 or MMP12 by contacting the cell with compounds that may inhibit IL-8 or MMP12 expression or activity, and determining whether IL-8 or MMP12 expression or activity has decreased. In particular, a person of skill in the art could screen for an agent that may inhibit IL-8 or MMP12 activity in a cell by providing a cell that has IL-8 or MMP112 activity, exposing the cell to a test agent, determining the IL-8 or MMP12 activity in the cell, and comparing the IL-8 or MMP12 activity to that of a control cell (the same type of cell as the exposed cell) not exposed to the test agent wherein a lower IL-8 or MMP12 activity in the exposed cell than that of the control cell indicates that the agent can reduce or inhibit IL-8 or MMP12 activity.

Administration of the IL-8 or MMP12 inhibitor and sunitinib to the patient can either be simultaneous, the IL-8 or MMP12 inhibitor can be administered before the sunitinib, or the sunitinib can be administered to the patient before the IL-8 or MMP12 inhibitor.

The present invention also includes using the IL-8 or MMP12 inhibitor and sunitinib in a method of treating a tumor in a useful warm blooded mammal who is susceptible to treatment and who is in need of treatment with an therapeutically effective amount of a IL-8 or a MMP12 inhibitor and sunitinib. The warm blooded mammal includes humans, farm animals such as horses, sheep, cattle, pigs and the alike as well as pets such as cats and dogs. It is preferred that the warm blooded mammal be a human.

In treating diseases or conditions in a warm blooded mammal, the IL-8 or MMP12 inhibitors and sunitinib of the invention can be used in combination or with other pharmaceutical agents useful in treating the disease or condition. Details of the administration of this combination of the IL-8 or MMP12 inhibitor and sunitinib are described further hereinbelow.

The present invention also includes a method of determining whether a tumor will respond to sunitinib therapy. More specifically, the method includes (a) providing a biological sample from an tumor, (b) detecting a level of IL-8 expression in the sample, and (c) comparing the IL-8 level in the sample to a suitable control. If the IL-8 expression level in the sample is elevated as compared to the control, then the renal cell tumor will not respond to sunitinib therapy. In one embodiment, the tumor is RCC.

The present invention also includes a method of determining whether a tumor will respond to sunitinib therapy. More specifically, the method includes (a) providing a biological sample from a tumor, (b) detecting a level of MMP12 expression in the sample, and (c) comparing the MMP12 level in the sample to a suitable control. If the MMP12 expression level in the sample is elevated as compared to the control, then the tumor will not respond to sunitinib therapy. In one embodiment, the tumor is RCC. A skilled artisan can readily set up suitable controls as reference points of comparison for the expression of IL-8 or MMP12. One suitable control is the median or average expression level of many renal cancer patients that are not resistant to sunitinib therapy. The larger the number of patients used to establish a median or average level of IL-8 expression as a control, the more accurate the diagnostic determination. Preferably, at least 25, 50, or 100 patients are used to establish the control level of expression. In one embodiment, the expression level of IL-8 or MMP12 in the sample is elevated at least 2-fold as compared to the level of IL-8 or MMP12 expression in the control, or at least 3-fold, 4-fold, or 5-fold as compared to the control.

IL-8 and MMP12 expression can be detected in normal or cancerous cells and tumor tissue. For example, one could assay IL-8 or MMP12 mRNA, or IL-8 or MMP12 protein in renal cells. A tagged antibody could be used to detect IL-8 or MMP12 by either immunoflurourescent or immunohistochemical staining. Alternatively, a tagged oligonucleotide probe complementary to a fragment of the nucleotide sequence of SEQ ID NO: 1 could be used to detect IL-8 mRNA and the nucleotide sequence of SEQ ID NO: 3 could be used to detect MMP12. In either case, both the number (percentage) of positive cells and the intensity of staining could be measured. Other methods of detecting IL-8 in a cell (e.g., a renal cell) could also be utilized. The levels of IL-8 or MMP12 protein and mRNA could be evaluated by Western and Northern blotting, respectively. Western blots could be quantitated by densitometric scanning of x-ray films. Northern blots could be hybridized to 32P-labeled probes for both IL-8 or MMP12 and GAPDH, bands quantitated by phosphorimaging, and IL-8 or MMP12 normalized to GAPDH in each sample sample. IL-8 mRNA levels could also be measured by quantitative reverse transcription—real time PCR using primers from within the nucleotide sequence of SEQ ID NO: 1. MMP12 mRNA levels could also be measured by quantitative reverse transcription—real time PCR using primers from within the nucleotide sequence of SEQ ID NO: 3.

Pharmaceutical Compositions and Kits:

In another embodiment, the present invention is a pharmaceutical composition of an IL-8 or MMP12 inhibitor and sunitinib. In said composition, the IL-8 or MMP12 inhibitor and sunitinib are dissolved in a pharmaceutically acceptable carrier or diluent, preferably an aqueous carrier. A variety of aqueous carriers or diluents can be used. These solutions are preferably sterile and generally free of undesirable matter. These compositions may be sterilized by conventional, well known sterilization techniques. Compositions may be formulated for injection, for example for direct injection to the site of intended treatment or intravenous injection.

Pharmaceutically acceptable carriers can contain a physiologically acceptable compound that acts, e.g., to stabilize the composition or to increase or decrease the absorption of the agent and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the adjunctive and cancer agents, or excipients or other stabilizers and/or buffers. Detergents can also used to stabilize the composition or to increase or decrease the absorption of the pharmaceutical composition.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the route of administration of the adjunctive anti-cancer agent and on the particular physio-chemical characteristics of the adjunctive anti-cancer agent.

The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that polypeptides, such as antibodies, when administered orally, may be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The composition of an IL-8 or MMP12 inhibitor and sunitinib of the invention can be delivered alone or as a pharmaceutical composition by any means known in the art, e.g., systemically, regionally, or, locally; by intraarterial, intratumoral, intravenous (IV), parenteral, intrapleural cavity, topical, oral, or local administration, as subcutaneous, intra-tracheal (e.g., by aerosol) or transmucosal (e.g., buccal, bladder, vaginal, uterine, rectal, nasal mucosa), intratumoral (e.g., transdermal application or local injection). Particularly preferred modes of administration include intraarterial injections, especially when it is desired to have a "regional effect," e.g., to focus specifically on the kidney.

Suitable doses or amounts of the IL-8 or MMP12 inhibitor and sunitinib will ultimately be at the discretion of the physician taking account of the nature of the condition to be treated and the condition of the patient. In general, dosage ranges will be 1 µg to 1 mg per kg body weight. The composition may be administered by any suitable route, e.g. by i.v. or i.p injection, or directly to the site of treatment.

The exact dosage and frequency of administration depends on the particular form of IL-8 or MMP12 inhibitor and sunitinib used, the particular tumor type being treated, the severity of the cancer being treated, the age, weight, general physical condition of the particular patient, other medication the individual may be using, and/or the patients response to the particular tumor being treated as is known to those skilled in the art. Physicians can monitor the progress of treatment by monitoring blood markers (e.g., IL-8 or MMP12) as well as the blood level of the IL-8 inhibitor, MMP12 inhibitor, or sunitinib as is known to those skilled in the art.

Also within the scope described herein is a kit for providing a therapeutically effective amount of bioactive agents for use in treating a patient, comprising a first container including a volume of IL-8 or MMP12 inhibitor stored within the container in substantially sterile form; a second container including a volume of sunitinib stored within the container in substantially sterile form; and instructions for using the IL-8 or MMP12 inhibitor and sunitinib to treat renal cell carcinoma. The kit can further contain at least one additional reagent.

Having now generally described the invention, the same will be more readily understood through reference to the following examples, which are provided by way of illustration, and are not intended to be limiting of the present invention, unless specified.

EXAMPLES

Example 1

Materials and Methods for Examples 2-9.

Reagents. SU11248 was provided by Pfizer Global Pharmaceuticals, and prepared as 20 mM stock solution in DMSO for in vitro studies.

Expression of RTKs in clear cell RCC. The mRNA expression of RTK-related genes was measured in 174 clear cell renal tumors and 15 normal kidney samples using Affymetrix HGU133 Plus 2.0 microarrays, as described elsewhere.

Cells and cell culture. ACHN, A-498, 786-O, 769-P, SW156, Caki-1, and Caki-2 RCC cell lines were obtained from the ATCC. UO-31, TK-10, SN12C, and RXF393 cells were kindly provided by Dr. George Vande Woude (Van Andel Research Institute); SKRC39 cells were obtained from Memorial Sloan-Kettering Cancer Center. The cells were maintained in DMEM or RPMI 1640 (Invitrogen) supplemented with 10% fetal bovine serum (FBS, Invitrogen), 100 IU/mL penicillin and 100 µg/mL streptomycin (Invitrogen) in a humidified incubator containing 5% CO2 at 37° C. Human umbilical vein endothelial cells (HUVEC), human lymphatic microvascular endothelial cells (HLMVEC) were obtained from Clonetics and maintained in Clonetics EBM-2 medium supplemented with EGM-2 singlequots or EGM-MV singlequots (Cambrex).

Ligand-dependent cell proliferation assay. RCC cells were plated in 96-well plates at a density of 3000 cells/well and starved in low serum overnight in a medium containing 0.1% FBS. Cells were treated with SU11248 and stimulated with 50 ng/ml recombinant human PDGF or VEGF, and cultured continuously in the presence of SU11248 for 72 h. Cell viability was assessed using the MTS assay (Promega). MTS assays were also performed on RCC cells growing in 10% FBS treated with SU11248. Results were expressed as percentage of viable cells relative to cells treated with DMSO. Experiments were performed in triplicate and repeated at least three times.

Soft agar colony formation assay. RCC cells were cultured in a two-layer agar system to prevent their attachment to the plastic surface. Cells (4×10$^4$) were trypsinized to single-cell suspensions, resuspended in 0.4% agar (Sigma), and added to a pre-set 1% bottom agar layer in 6-well plates. The top agar cell layers were covered with culture medium containing 10% FBS and either SU11248 (1, 2.5, and 5 µM); 0.1% DMSO; or were left untreated. The top medium containing inhibitors was changed twice per week. Cells were incubated in 5% CO2 at 37° C. for 14 d, and colonies were stained with 0.005% crystal violet in methanol. The colonies with a diameter exceeding 100 µm were counted on micrographs using ImageJ v1.37v software. Experiments were performed in triplicate and repeated three times.

Immunoprecipitation and immunoblotting. RCC cells were starved in low serum (0.1% FBS) overnight before treatment with SU11248 for 2 h. After treatment, cells were stimulated with 50 ng/ml recombinant human PDGF or VEGF (R&D Systems) for 10 min. Cells were then lysed with HNTG lysis buffer (50 mM HEPES, 150 mM NaCl, 10% glycerol, 1% Triton X-100, 1.5 mM MgCl2, and 1 mM EGTA) containing protease and phosphatase inhibitors [10 mM sodium fluoride, 1 mM sodium orthovanadate, and protease inhibitor cocktail (Roche Diagnostics)], and protein concentration was determined using the Dc protein assay according to the manufacturer's instructions (Bio-Rad). One mg of protein from each sample was immunoprecipitated overnight at 4° C. with an anti-PDGFR (SC-432; Santa Cruz Biotechnology) and anti-VEGFR (2479; Cell signaling) antibody and protein G/A agarose beads (Pierce). Immune complexes were washed with HNTG lysis buffer containing inhibitors. Proteins were eluted by boiling in SDS sample buffer, separated by SDS-PAGE, and transferred to nitrocellulose membranes. Membranes were probed with an anti-phosphotyrosine antibody (4G10; Upstate) and then stripped with stripping buffer. To detect total PDGFR and VEGFR levels, membranes were reprobed with the same anti-PDGFR and anti-VEGFR antibody that was used for the immunoprecipitation. Western blot analysis of phospho-ERK1/2 (9106; Cell Signaling), phospho-Akt (4051; Cell Signaling), and phospho-mTOR (2971; Cell Signaling) was performed on whole cell lysates (40 µg) as described above.

Xenograft Models.

Tumor implantation and growth. All animal studies were in compliance with VARI Institutional Animal Care and Use Committee (IACUC) policies. Six-week-old female BALB/c nu/nu nude mice (Charles River) were given subcutaneous injections of 3×106 ACHN or SN12C cells in the right flank. Tumor size was measured twice per week using digital calipers (Mitutoyo) with an accuracy of ±0.02 mm, and tumor volume was calculated as length×width×height×0.5. Tumor growth ratio is presented as mean±SD and normalized to the initial volume when treatment began. When tumors had grown to an average volume of 200 mm3 tumor-bearing mice were separated into four groups of ten animals. Three treatment groups received an oral gavage of SU11248 as a citrate buffered (pH 3.5) solution once daily through the end of the study, at the dosages of 20 mg/kg, 40 mg/kg, 80 mg/kg, respectively. At the same time, one vehicle control group received citrate buffer (pH 3.5) only. Mice were euthanized at the end of the treatment period. Plasma samples were collected and stored at −80° C. for further studies. Tumors were removed, cleaned from adjacent tissues, fixed in 4% polyformadehyde and paraffin-embedded, and then 4-µm-thick sections were prepared. Some sections were stained with H&E and the others were used for subsequent immunohistochemical analysis.

Target modulation study. In vivo target modulation studies to determine the effect of inhibitor treatment on the phosphorylation of target RTKs expressed on tumor cells were performed as described (13, 22). Briefly, implanted tumor cells expressing PDGFR and VEGFR were allowed to grow untreated to a size of 300-500 mm3. Mice were then administered a single oral dose of SU11248 at the indicated concentration. At the indicated time after dosing, individual mice were sacrificed, their tumors resected. Resected tumors were homogenized and lysed in cold HTNG buffer. Total PDGFR and VEGFR were immunoprecipitated from individually lysed tumors, and the amount of phosphorylated and total RTK in each sample determined by Western blot analysis. The extent of phosphorylation in tumors resected from SU11248-treated animals was typically compared with that in tumors resected from untreated or vehicle-treated animals, either predose or at the same time point, based on visual inspection of films after Western blot analysis.

Immunohistochemistry (IHC). Sections from the formalin-fixed, paraffin-embedded tumor tissues were cut to 4 µm and deparaffinized in xylene, followed by treatment with a graded series of ethanol solutions and rehydration in PBS. The proliferative index of tumor sections was determined by staining with a rabbit polyclonal PCNA antibody (Abcam). Briefly, sections were immersed in 0.3% hydrogen peroxide to block endogenous peroxidase activity and then incubated in 5% goat serum. The sections were then incubated with PCNA antibody overnight at 4° C. in primary antibody diluting buffer (Biomeda). After washing with TTBS, sections were incubated with biotinylated secondary antibodies (Vector). After washing with TTBS, sections were incubated with Vectastain ABC reagent (Vector). The immune complex was visualized using DAB substrate solution (Vector). To determine the apoptotic index, TUNEL staining was also performed on tumor sections according to the protocol of the manufacturer (Roche Diagnostics). CD34 (MEC 14.7, Abcam) staining was performed as described elsewhere.

For PCNA and TUNEL staining, pictures of five fields (0.09 mm2 each) per slide were taken using a Nuance multispectral imaging system (CRi) at 400× magnification and multispectral acquisition software. The images were processed by Nuance image processing software 1.6.8 to measure the spectral absorbance curve of each of the stains and then were unmixed. The percentage of positive staining (DAB) was then quantified using Imagine_0.16 software (developed by the inventors lab) and expressed as the percentage of positive pixels to total pixels of the analyzed area. For CD34 staining, pictures of five fields per slide were taken at 200× magnification. Microvessel density (MVD, CD34 positive) and was determined in a blinded manner by counting using Imagine_0.16, for each tumor, the total number of vessels in five fields (0.36 mm2 each) showing the highest vascular density 8.

Cytokine screening. RCC cells were seeded to 6-well plates and treated with SU11248 at indicated concentrations or DMSO, or left untreated. Conditioned culture medium was collected after 24 h treatment, and cells were lysed to determine total protein concentration. Conditioned medium (CM) from RCC cell culture and plasma samples from xenograft study were sent to Rules-Based Medicine for cytokine screening (human MAP service version 1.6, 89 antigens). The results for CM were normalized to total protein concentration.

Resistance study. Resistant tumors were established by mimicking human dosing schedule (3 weeks on and 3 weeks off), and tumors that did not respond to the 2nd round SU11248 treatment were considered resistant. Mice were sacrificed after the 2nd round SU11248 treatment, and plasma samples were collected. The MVD was analyzed for resistant, sensitive, and control tumors. The plasma samples were also sent for cytokine screening.

Statistical analysis. All values are expressed as mean±standard deviation. Values were compared using Student-t test. P<0.05 was considered significant.

Example 2

PDGFR-β and VEGFR-2 are Highly Expressed in Human ccRCC.

Figure 1A:
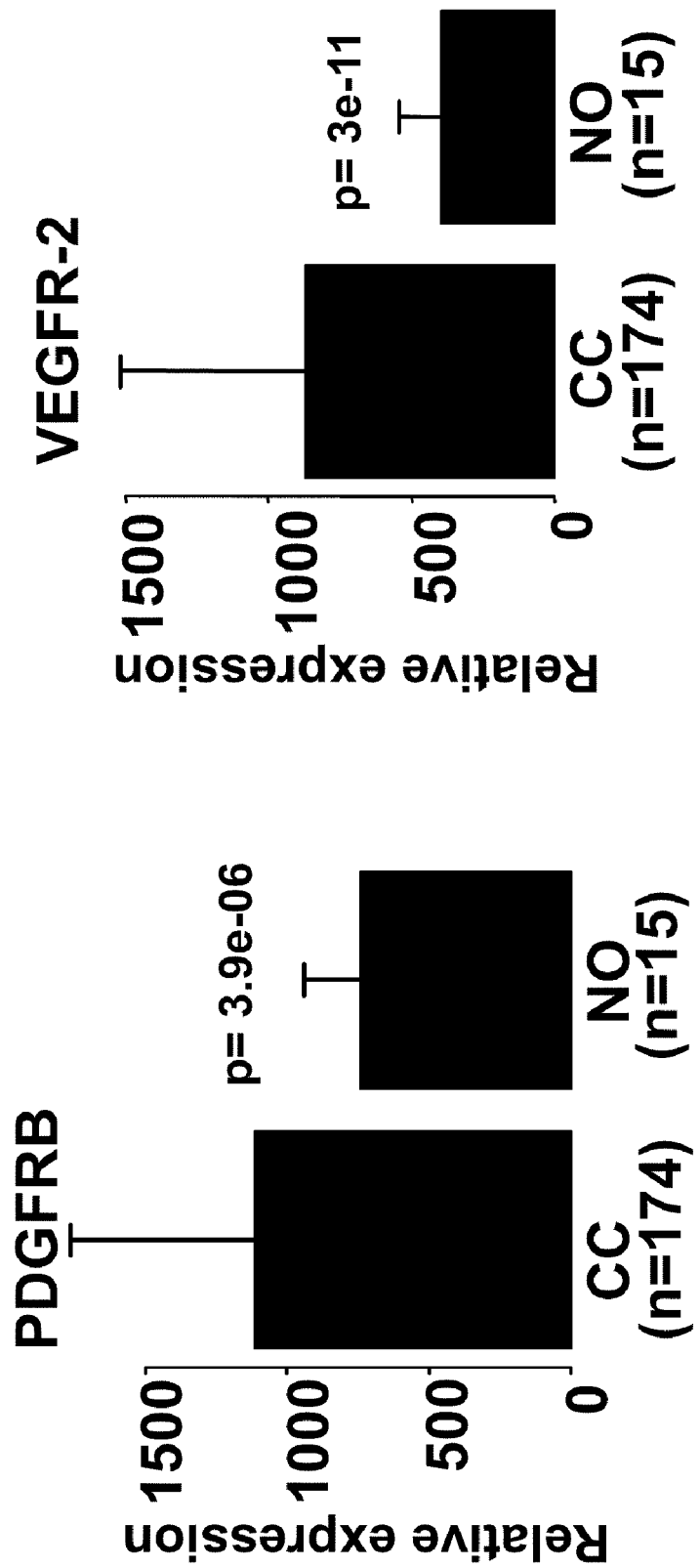
FIGS. 1A and 1B show overexpression of PDGFR-β and VEGFR-2 in human ccRCC.
Figure 1B:
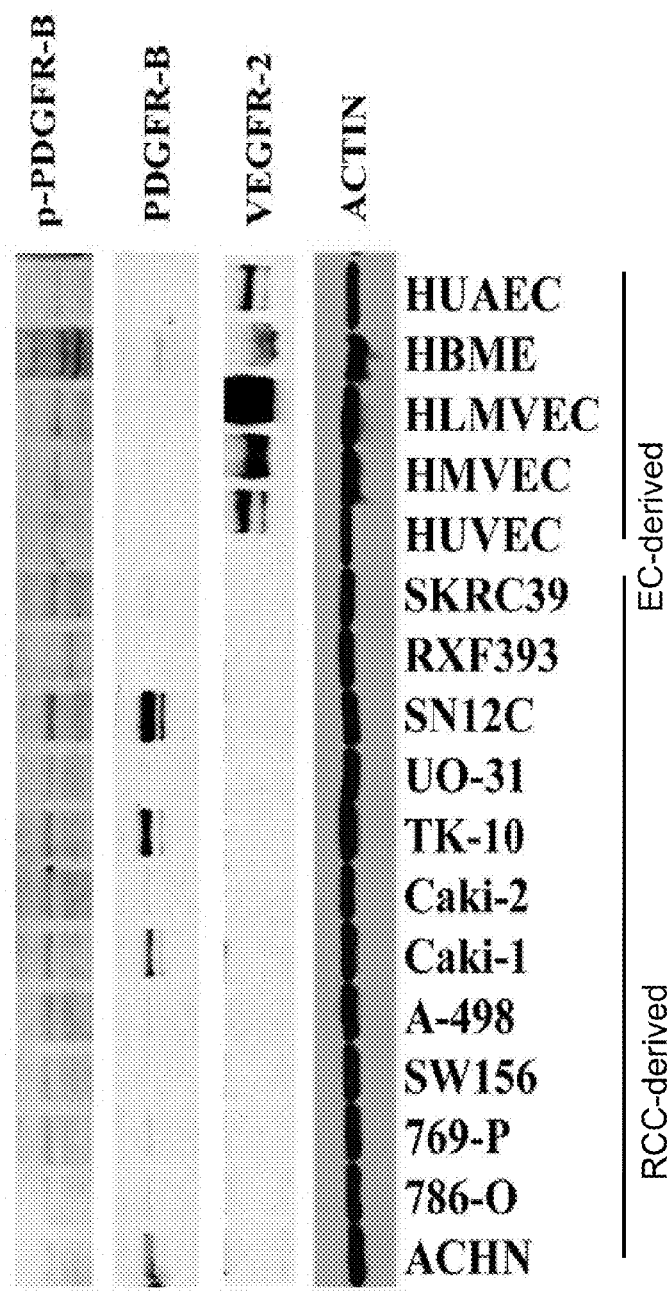

To date, no somatic mutations were found on PDGDR, VEGFR, FLT3, c-KIT, and RET kinases in human RCC9. To find out which RTK(s) are SU11248's targets to treat RCC patients, the inventors first examined the expression profile of these RTKs in 174 human clear cell RCC samples by Affymetrix microarray analysis. The inventors found that PDGFR-β and VEGFR-2, but not others were highly expressed in human ccRCC compared with normal controls (P<0.001, FIG. 1A). To confirm this result, the inventors also examined the expression and activation of the RTKs in RCC cell lines by Western blotting. No significant activation of these RTKs in RCC cells was detected, comparing with the endothelial cell controls. PDGFR-β was expressed by 4 of 12 RCC cell lines, and VEGFR was expressed only by endothelial cell lines (FIG. 1B). FLT3, c-KIT, and RET expression were undetectable in these RCC cell lines. Based on the expression profile, the inventors hypothesized that SU11248 inhibited the growth of the tumors by suppressing the PDGFR and VEGFR signalings in RCC.

Example 3

SU11248 Inhibits PDGFR Signaling Pathways in RCC Cells in Vitro.

Figure 2A:
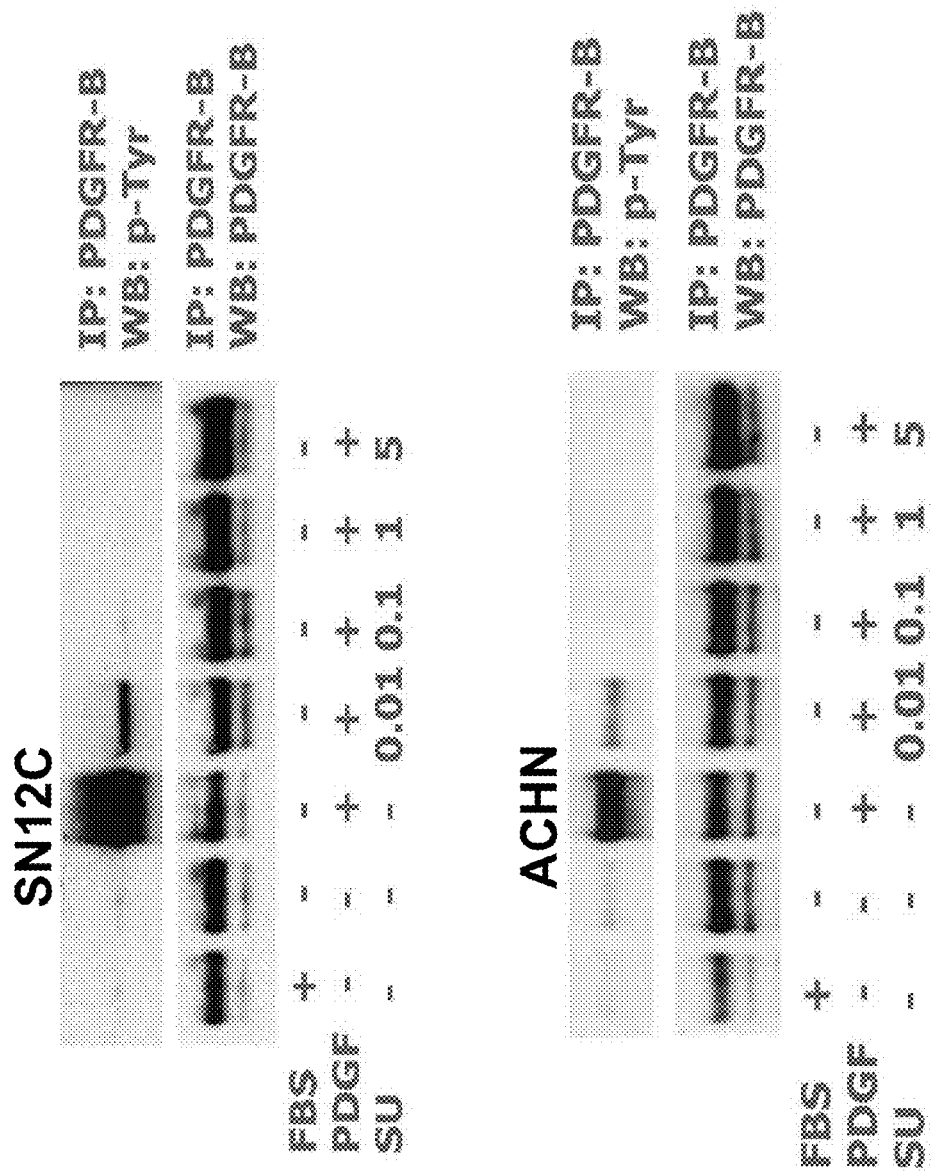
FIGS. 2A and 2B show SU11248 inhibited phosphorylation of PDGFR and downstream signaling in RCC cells.

First, the inventors examined the effect of SU11248 on the activation of RTKs in RCC cells by IP and Western Blotting. Two PDGFR-expressing cell lines SN12C and ACHN were chosen to evaluate whether SU11248 could inhibit the phosphorylation of PDGFR-β in vitro. SU11248 decreased PDGF-stimulted phosphorylation of PDGFR-β at 0.01 μM in both cell lines and completely inhibited the phosphorylation of PDGFR-β from 0.1 μM (FIG. 2A). Although VEGFR-2 is expressed in these 2 cell lines, the inventors could not detect phosphorylated VEGFR-2 signals with VEGF stimulation. So next the inventors mainly focused on the effect of SU11248 on PDGFR signaling pathways.

Figure 2B:
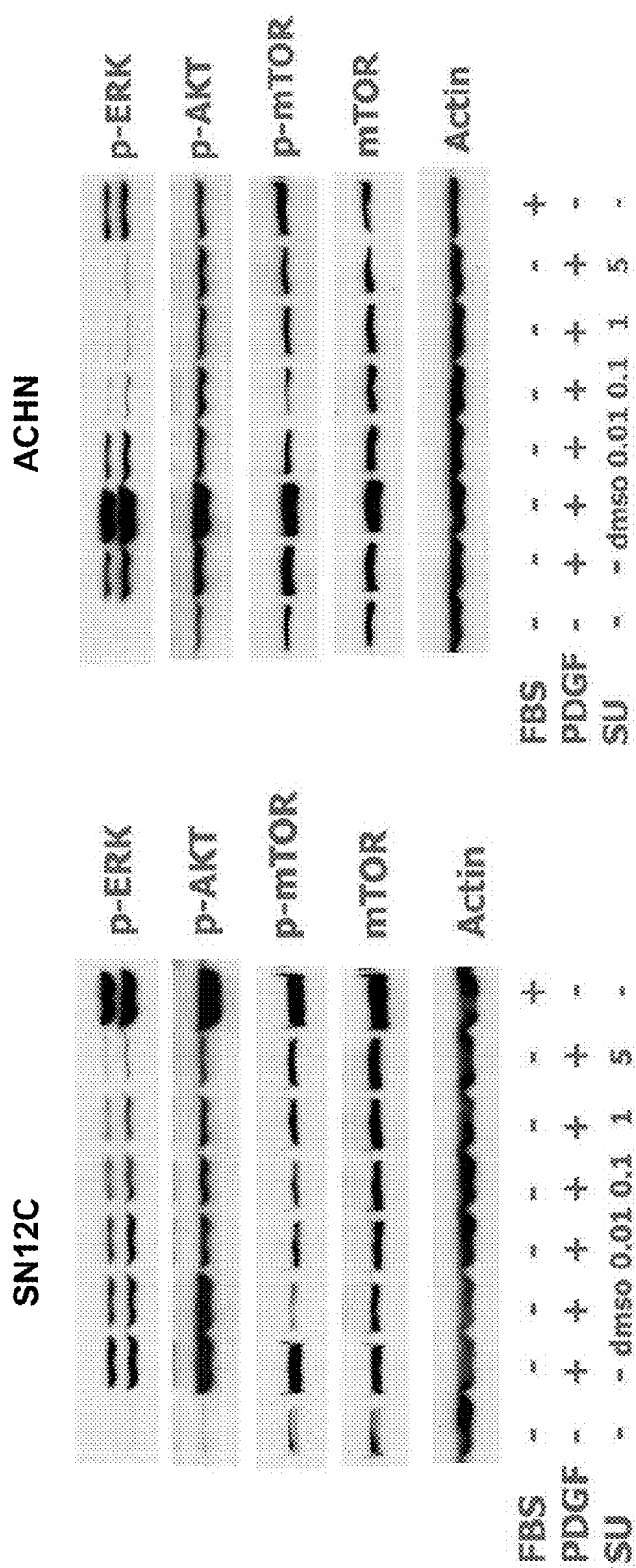

RTKs transduce signals of proliferation, migration and survival from the extracellular environment into the cells through downstream cascades. Then the inventors tested the effect of SU11248 on downstream signaling pathways of PDGFR. ERK and Akt were two main downstream effectors in PDGFR signaling pathways 10, 11. Western blot analysis showed that SU11248 inhibited PDGF-stimulated activation of ERK, Akt and mTOR at ~0.1 μM, at which SU11248 could significantly inhibit the activation of PDGFR (FIG. 2B).

Example 4

Much Higher Concentrations of SU11248 were Required to Inhibit Proliferation than to Suppress PDGFR Signaling Pathways in RCC Cells.

As PDGFR/ERK and PDGFR/Akt pathways play an essential role in cell proliferation and survival, the inventors examined the effect of SU11248 on proliferation of RCC cells in both PDGF-only and complete mediums. In both conditions, the IC50s of SU11248 to RCC cell lines were similar, at ~4-10 μM, which were much higher than that required to inhibit the phosphorylation of PDGFR-β (0.1 μM). SU11248 showed minimal effect on the proliferation of RCC cells at 0.1 μM, although at which the phosphorylation of PDGFR-β was suppressed. This result indicates that inhibition of PDGFR signaling pathway is not sufficient to inhibit the proliferation of RCC cells in vitro.

To further explore the role of PDGFR signaling pathways in RCC cells in vitro, the inventors first starved the cells and then activated the PDGFR signaling pathways with PDGF. To the inventors surprise, while FBS could stimulate the proliferation of RCC cells, PDGF alone could not stimulate the proliferation of RCC cells (FIG. 3), although it has been reported that PDGF could stimulate the proliferation of PDGFR-transfected NIH-3T3 cells 12. This indicates that the proliferation of RCC cells in vitro does not rely on PDGFR signaling pathways.

Example 5

SU11248 Inhibited Anchorage-Independent Growth of RCC Cells at Higher Concentrations.

Anchorage-independent growth is a characteristic of transformed cells. Using soft agar colony formation assay, the inventors next evaluated whether SU11248 could reverse the transforming potential of RCC cells at the concentration inhibiting the PDGFR signaling pathways. Although SU11248 significantly inhibited the anchorage-independent colony formation of ACHN and SN12C cells at higher concentration (5 μM), it showed minimal effect on ACHN and SN12C cells at 1 μM, at which SU11248 could completely inhibited the activation of PDGFR signaling pathways (FIG. 4). These results are consistent with the proliferation assays.

Example 6

SU11248 Inhibited VRGFR-2 Signaling Pathways in Endothelial Cells in Vitro.

Since VEGFR is also expressed and activated in tumor-associated endothelial cells, the inventors next investigated the effect of SU11248 on endothelial cell lines in vitro. First the inventors examined the expression of the RTKs in 5 endothelial cell lines. VEGFR-2 was highly expressed in those cell lines; PDGFR expression was weak or undetectable. Then the inventors detected the inhibition of phosphorylation of VEGFR in endothelial cell lines by SU11248 using IP and Western blot. SU11248 could inhibit the phosphorylation of VEGFR in HLMVEC cells at similar concentration (0.01-0.1 μM) to the inhibited phosphorylation of PDGFR in RCC cells. Downstream of VEGFR signaling pathways, such as ERK, was also inhibited by SU11248 at this low concentration (FIG. 5A).

Example 7

SU11248 Inhibited Endothelial Cells Proliferation when VEGFR-2 Signaling was Abrogated.

The direct effect of SU11248 on endothelial cell proliferation in vitro was analyzed by MTS assay. Comparing with RCC tumor cells, SU11248 showed more robust inhibitory effects on the proliferation of HUVEC and HLMVEC cells. IC50s for endothelial cell lines under VEGF-dependent conditions were about 0.01 μM, which was identical to the concentration for inhibiting the activation of VEGFR (FIG. 5B), although in complete medium the IC50s for endothelial cells were about 6 μM, which was similar to those for RCC cell lines, and much higher than that for target inhibition. After serum starvation, VEGF alone could stimulate the growth of endothelial cells. These results demonstrated that VEGFR signaling is required for proliferation of endothelial cells and inhibition of VEGFR signaling with SU11248 suppresses growth of endothelial cells.

Example 8

SU11248 Inhibited RCC Tumor Growth in Vivo.

Next the inventors used xenograft model to investigate the effect of SU11248 in vivo. The inventors tested the effect of SU11248 on established tumors after subcutaneous inoculation of the cancer cells in the right flank of nude mice. Treatment began when tumor volume reached 200 mm3 with daily oral gavages of 3 dosages of SU11248 in a citrate buffer solution. SU11248 showed growth inhibition (40 mg/kg) or stasis (80 mg/kg) effect on SN12C xenografts, whereas showed growth inhibition at 20 mg/kg and regression at 40 and 80 mg/kg on ACHN xenografts (FIG. 6A).

The inventors observed extensively necrotic areas in SU11248-treated tumor sections. Therefore, the inventors examined the effect of SU11248 on RCC cell proliferation and apoptosis in vivo by PCNA and TUNEL staining. For SN12C xenografts, the proliferation index (shown as the percentage of PCNA-positive cells) did not change after SU11248 treatment when compared with vehicle controls (FIG. 6B). Extensive DNA fragmentation may occur in late stages of necrosis, which would also be positive in TUNEL staining 13, 14. So the inventors only count TUNEL-positive cells in the viable tumor section to calculate the percentage of apoptosis induced by SU11248 in vivo. In SN12C xenografts, no significant increase of apoptotic cells (as shown by apoptosis index) was found after SU11248 treatment (FIG. 6B). This result suggests that SU11248 inhibited the tumor growth in vivo mainly by suppressing the neovascularization.

Example 9

SU11248 Inhibited RCC Tumor Angiogenesis in Vivo.

To confirm the effect of SU11248 on tumor endothelium in vivo, the inventors used CD34, a vascular endothelial cell biomarker, to stain the tumor sections and counted the microvessel density (MVD). The MVD was significantly decreased with SU11248 treatment when compared with vehicle controls ($P<0.001$, FIG. 7). This result indicates that SU11248 inhibited the growth of RCC tumors in vivo by suppressing the tumor angiogenesis.

Example 10

Materials and Methods for Examples 11-15

Reagents: Sunitinib was provided by Pfizer Global Pharmaceuticals. The monoclonal IL-8 neutralizing antibody was purchased from R & D (MAB208). The mouse IgG control was obtained from Innovative Research (IR-MS-GF).

Cells and Cell Culture

A-498 and 786-O RCC cell lines were obtained from the ATCC. SN12C cells were kindly provided by Dr. George Vande Woude (Van Andel Research Institute). The cells were maintained in DMEM or RPMI 1640 (Invitrogen) supplemented with 10% fetal bovine serum (FBS, Invitrogen), 100 IU/mL penicillin, and 100 µg/mL streptomycin (Invitrogen) in a humidified incubator containing 5% $CO_2$ at 37° C.

Xenograft Models

Establishment of Sunitinib Resistant Xenograft Model

All animal studies were in compliance with VARI Institutional Animal Care and Use Committee (IACUC) policies. Both VHL-mutated A-498 (vhl−/−), 786-O (vhl−/−), and VHL-wild type SN12C (vhl+/+) cells were chosen for the resistance study to clarify the possible influence of VHL status on sunitinib response. Six-week-old female BALB/c nu/nu nude mice (Charles River) were given subcutaneous injections of $3 \times 10^6$ A-498, 786-O, or SN12C cells in the right flank. Tumor size was measured twice per week using digital calipers (Mitutoyo) with an accuracy of ±0.02 mm, and tumor volume was calculated as length×width×height×0.5. Tumor growth ratio is presented as mean±standard deviation and normalized to the initial volume when treatment began. sunitinib-resistant tumors were established in xenograft model using 2 dosing strategies. To directly mimic the treatment regimen for human ccRCC (4 weeks on and 2 weeks off), we treated A-498 and SN12C xenograft mice with an intermittent dosing schedule (3 weeks on and 3 weeks off), and tumors that showed phenotypic resistance during the 1st (no response at all) or 2nd round (stopped responding after an initial growth inhibition) of sunitinib treatment were considered resistant. On the other hand, another dosing strategy of sunitinib, which is continuous daily gavage without break, was also applied to 786-O xenografts since the majority of these tumors developed resistance by the end of the 1st round sunitinib treatment. Xenograft tumors that either didn't respond to treatment or progressed on treatment after an initial response were considered phenotypic resistance.

Sunitinib was administered by oral gavage as a citrate buffered (pH 3.5) solution once daily, at the dosages of 40 mg/kg (for A-498 and 786-O xenografts), or 80 mg/kg (for SN12C xenografts), respectively. At the same time, one vehicle control group received citrate buffer (pH 3.5) only. Plasma samples were collected before and during the course of sunitinib treatment and stored at −80° C. for further studies.

Neutralizing IL-8 Antibody Treatment

To study the reversal of sunitinib resistance by neutralization of IL-8 activity, 786-O tumor bearing mice showing phenotypic resistance to sunitinib were randomly divided into 2 groups; one group continually receiving sunitinib plus control IgG treatment, the other group receiving sunitinib plus IL-8 neutralizing antibody at 100 µg per mouse through intraperitoneal injection every other day for a total of 8 times. The monoclonal IL-8 neutralizing antibody was purchased from R&D (MAB208). The mouse IgG control was obtained from Innovative Research (IR-MS-GF).

For A-498 tumor bearing mice which were on 3-week-on and 3-week-off sunitinib treatment schedule, during the course of 2nd round sunitionib treatment, neutralizing IL-8 monoclonal antibody was added to sunitinib regimen to one group of mice whose tumors continued growing 20% over the initial volume when 2nd round treatment began. At the same time, the other 2 groups of resistant mice receiving sunitinib only or IL-8 antibody only were also maintained as comparison. IL-8 neutralizing antibody or control IgG was delivered by ip injection every other day for a total of 7 times.

Twenty-four hours after the last treatment, tumors were removed, cleaned from adjacent tissues, fixed in 4% paraformaldehyde and paraffin-embedded, and then 4-µm-thick sections were prepared. Some frozen sections were also prepared. Some sections were stained with H&E and the others were used for subsequent immunohistochemical analysis.

Immunohistochemistry (IHC)

The microvessel density (MVD) was analyzed in sections of resistant, sensitive, and control tumors by CD34 staining. Sections from the formalin-fixed, paraffin-embedded tumor tissues were cut to 4 µm and deparaffinized in xylene, followed by treatment with a graded series of ethanol solutions and rehydration in PBS. To assess MVD, CD34 (MEC 14.7, Abcam) staining was performed as described [7]. Briefly, sections were immersed in 0.3% hydrogen peroxide to block endogenous peroxidase activity and then incubated in 5% goat serum. The sections were then incubated with CD34 antibody (1:50) overnight at 4° C. in primary antibody diluting buffer (Biomeda). After washing with TTBS, sections were incubated with biotinylated secondary antibodies (Vector). After washing with TTBS, sections were incubated with Vectastain ABC reagent (Vector). The immune complex was visualized using DAB substrate solution (Vector). For quantification of MVD, pictures of five fields (0.36 mm2 each) per slide were taken using a Nuance multispectral imaging system (CRi) at 200× magnification and multispectral acquisition software. The images were processed by Nuance image processing software 1.6.8 to measure the spectral absorbance curve of each of the stains and then were unmixed. The percentage of positive staining (DAB) was then quantified using Imagine_0.16 software (developed by the inventors lab) and expressed as the percentage of positive pixels to total pixels of the analyzed area. MVD was determined in a blinded manner by counting for each tumor, the total number of vessels in five fields showing the highest vascular density.

The IHC staining for IL-8 (sc-7922, Santa Cruz) on human ccRCC sections was performed at Cleveland Clinic. The 20 human ccRCC tumor samples were from both Spectrum Health and Cleveland Clinic.

Cytokine Screening

The plasma samples collected from resistant, sensitive, and control tumor-bearing mice were screened though antibody array analysis (Rules-Based Medicine, RBM) Plasma samples were sent to RBM for cytokine screening (human MAP service version 1.6, 89 antigens).

IL-8 ELISA

The IL-8 level in plasma from xenograft mice was determined using an ELISA kit (D8000C, R & D system).

Statistical Analysis

All values are expressed as mean±standard deviation. Values were compared using Student-t test. $P<0.05$ was considered significant.

Example 11

Reacquisition of Angiogenesis and Elevated Plasma IL-8 Level are Associated with Sunitinib-Resistant Phenotype in an Intermittent Dosing Animal Model.

To establish a sunitinib resistant xenograft model, the inventors first used a 3-weeks-on and 3-weeks-off dosing strategy, which mimicked the clinical regimen (4-weeks-on and 2-weeks-off) given to patients with metastatic ccRCC with modification. A-498 xenografts were treated with 40 mg/kg sunitinib, and SN12C xenografts were treated with 80 mg/kg sunitinib as these doses were identified as the minimal required dosage to induce stable disease in the inventors preliminary studies (data not shown). Using this approach, 38% (13/34) of all treated A-498 xenograft mice and 33% (4/12) of all treated SN12C xenograft mice showed phenotypic resistance, either did not respond initially or progressed after an initial response at the same doses of sunitinib during the 2nd round treatment, to sunitinib. As shown in FIG. 1, a subset of SN12C xenografts when treated with 80 mg/kg sunitnib was resistant to the 1st or 2nd round treatment, and a portion of A-498 xenografts when treated with 40 mg/kg sunitinib was resistant to the 1st or 2nd round treatment. This pattern of response directly mimics the clinical response to sunitinib treatment in ccRCC patients.

To explore the mechanism underlying this resistance, the inventors first ruled out the possibility of target mutations by sequencing a panel of RTK genes. No mutations in the following RTKs: FLT1 (VEGFR-1), KDR (VEGFR-2), FLT4 (VEGFR-3), PDGFR-α, PDGFR-β, FLT3, c-KIT, and RET, were identified in the resistant, sensitive, control SN12C xenograft tumors or in the parental cell line. Since the inventors previous study has shown that sunitinib exhibits its antitumor effect on ccRCC mainly through suppression of tumor angiogenesis in vivo, the inventors evaluated the features of the tumor vasculature both in the sensitive and resistant xenograft tumors. The MVD in the sunitinib-resistant SN12C and A-498 tumors was significantly higher than that found in the sensitive tumors ($p<0.05$). These results are consistent with the notion that sunitinib-induced growth inhibition is mainly through effects on VEGFR-mediated vascularization. Moreover, sunitinib resistance is mediated through an escape from anti-angiogenesis in which neovacularization is possibly reactivated through a VEGF/VEGFR-independent mechanism.

To determine if vascularization of sunitinib resistance tumors was associated with VEGF-independent mechanism, the inventors screened the plasma from mice containing SN12C xenografts that were sensitive or resistant to sunitinib for changes in association with secreted angiogenic factors. Analysis of cytokines and pro-angiogenic factors using human antibody arrays showed that plasma levels of IL-8, which is a potent pro-angiogenic, but not VEGF and bFGF, among 89 screened cytokines were higher in resistant tumors compared with sensitive tumors. This result was also confirmed by an ELISA assay in both SN12C and A-498 xenografts ($p<0.05$). This result suggests that plasma IL-8 level may be a useful biomarker for sunitinib response.

Example 12

Reacquisition of Angiogenesis and Elevated Plasma IL-8 Level is Associated with the Sunitinib-Resistant Phenotype in a Continuous Dosing Animal Model.

The inventors next use continuous dosing strategy in 786-O xenograft model since the majority of these tumors (15/18, 83%) developed resistance by the end of the 1 st round sunitinib treatment. 786-O xenograft tumors were treated with sunitinib continuously for 52 days. Response to sunitinib was presented in 2 phase: SU-responding phase (17 days, Day 33 to Day 50), in which the tumor presented stable disease with treatment (tumor growth ratio 1.09 on Day 50), similar to ccRCC patient response to sunitinib; and SU-resistant phase (Day 50 to Day 67), in which the tumor progressed with treatment (tumor growth ratio 1.83 on Day 67), $P<0.01$).

To verify if the resistance was also associated with tumor reangiogenesis and elevated plasma IL-8 level, the inventors examined the MVD of sunitinib treated tumor and plasma IL-8 level from the tumor bearing mice. The MVD in the sunitnib-resistant 786-O tumors was significantly higher than that found in the sensitive tumors ($p<0.05$). Plasma levels of IL-8 were also higher in resistant tumors compared with sensitive tumors as analyzed by an ELISA assay ($p<0.05$).

Example 13

Neutralizing of IL-8 Activity Resensitizes ccRCC Tumors to Sunitinib Treatment.

To further explore if the elevation of IL-8 level functionally contributes to sunitinib resistance, the inventors added an IL-8 neutralizing monoclonal antibody to sunitinib treatment regimen when the RCC xenografts showed phenotypic resistant to sunitinib. A-498 tumor bearing mice were given sunitinib treatment daily on a 3-week-on and 3-week-off schedule. Roughly a 38% (13/34) of all treated mice showed phenotypic resistance to sunitinib during the 2nd round treatment. These resistant mice were randomly divided into 3 groups, one group receiving sunitinib treatment alone (n=4), the second group receiving IL-8 neutralizing antibody treatment alone (n=5), the third group receiving sunitinib plus IL-8 antibody treatment (n=4) at the indicated dosage and interval specified in Example 10. The resistant tumors started to respond to sunitinib treatment again with the addition of the neutralizing IL-8 antibody, while neither treatment alone had this effect (FIGS. 8A and 8B). For the continuous dosing xenograft model, 83% (15/18) of all treated mice showed phenotypic resistance to sunitinib during treatment. As shown in FIGS. 8C and 8D, starting from Day 68 SU-resistant 786-O xenograft mice were randomly divided into 2 groups, one group receiving sunitinib plus IL-8 neutralizing antibody (n=7), the other group receiving sunitinib plus control IgG (n=8) at the indicated dosage and interval specified in Example 10. Sunitinib plus IL-8 antibody treatment inhibited tumor growth compared to sunitinib treatment alone (with control IgG). The neutralizing activity of IL-8 antibody was confirmed by reduced plasma level of IL-8 in response to treatment. After the combination treatment stopped, some mice from the sunitinib and control IgG treatment group were divided into 2 subgroups, one subgroup receiving sunitinib treatment alone (n=2), the other subgroup receiving IL-8 antibody treatment alone (n=3). IL-8 treatment alone did not have any effect on tumor growth of these sunitinib resistant mice similar as sunitinib treatment (FIG. 8E). These results indicate that RCC cells bypassed the angiogenic inhibition of sunitinib by upregulation of compensatory pro-angiogenic factors, i.e. IL-8, which contributed to sunitinib-resistance and may be targeted for subsequent treatment.

Example 14

Elevated IL-8 is also Found in Sunitinib-nonresponsive ccRCC Patients.

Figure 9:
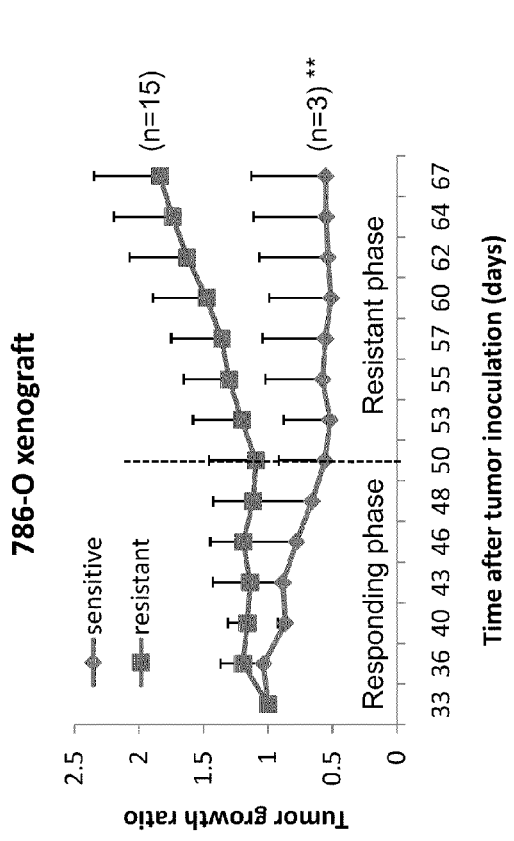
Figure 9:
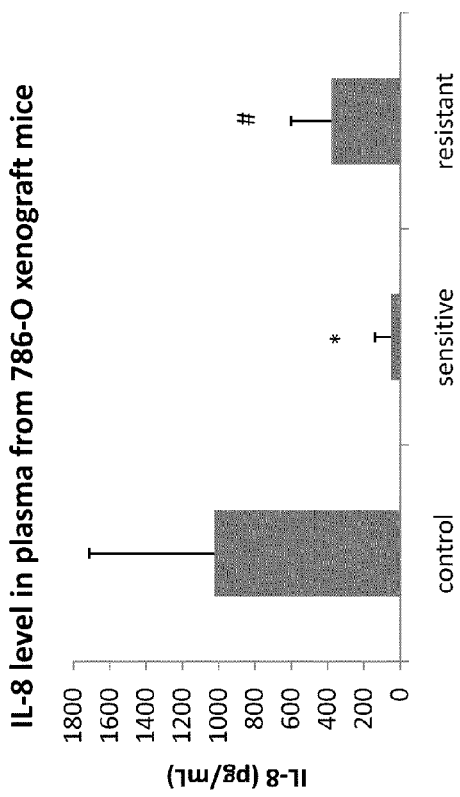

To confirm the inventors findings in animal model are consistent with human setting, the inventors examined the expression of IL-8 in tumor samples from untreated ccRCC patients who later underwent sunitinib treatment and showed different responses (either responsive or refractory) by IHC staining (n=20). Patient response to sunitinib was evaluated by RECIST criteria. Tumors from patients who later progressed while on sunitinib treatment (n=9) had strong IL-8 expression, while tumors from patients who did not progress on sunitinib treatment (n=11) only had focally weak IL-8 expression (FIG. 9). These results indicate that IL-8 expression level could be a useful marker to predict response to sunitinib in a larger patient population.

Similar to IL-8, MMP12 has a pattern of expression correlating with resistance: in both xenograft and human cases. It is not assayable in the serum of the resistance mice. The cDNA and amino acid sequences for MMP12 are shown in the attached Sequence Listing identified as SEQ ID NOS. 3 and 4, respectively.

Example 15

Neutralizing IL-8 Activity Doesn't Affect the Growth of Treatment-naïve Xenograft Tumors.

The inventors study indicated that there might be a switch in angiogenic signaling from VEGF dependence to IL-8 dependence in the face of VEGF/VEGFR inhibition in ccRCC. To test if pro-angiogenic IL-8 signaling also plays a role in treatment-naïve tumor, the inventors examined the effect of IL-8 inhibition on these tumors. Neutralizing of IL-8 activity alone could not inhibit growth of A-498 and 786-O xenograft tumors in vivo compared to sunitinib treatment alone or the combination of sunitinib and IL-8 antibody treatment.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

Those skilled in the art will recognize, or be able to ascertain using no more than routine experimentation, many equivalents to the specific embodiments of the invention described herein. Such equivalents are intended to be encompassed by the following claims.

REFERENCES

1. Jemal, A., et al. Cancer statistics, 2008. CA Cancer J Clin 58, 71-96 (2008).
2. Rini, B. I. Temsirolimus, an inhibitor of mammalian target of rapamycin. Clin Cancer Res 14, 1286-1290 (2008).
3. de Mulder, P. H., et al. [Angiogenesis inhibitors for the systemic treatment of metastatic renal cell carcinoma: sunitinib, sorafenib, bevacizumab and temsirolimus]. Ned Tijdschr Geneeskd 152, 371-375 (2008).
4. Rock, E. P., et al. Food and Drug Administration drug approval summary: Sunitinib malate for the treatment of gastrointestinal stromal tumor and advanced renal cell carcinoma. Oncologist 12, 107-113 (2007).
5. Kane, R. C., et al. Sorafenib for the treatment of advanced renal cell carcinoma. Clin Cancer Res 12, 7271-7278 (2006).
6. Escudier, B., et al. Sorafenib in advanced clear-cell renal-cell carcinoma. N Engl J Med 356, 125-134 (2007).
7. Furge, K. A., et al. Detection of DNA copy number changes and oncogenic signaling abnormalities from gene expression data reveals MYC activation in high-grade papillary renal cell carcinoma. Cancer Res 67, 3171-3176 (2007).
8. Murphy, D. A., et al. Inhibition of tumor endothelial ERK activation, angiogenesis, and tumor growth by sorafenib (BAY43-9006). The American journal of pathology 169, 1875-1885 (2006).
9. Greenman, C., et al. Patterns of somatic mutation in human cancer genomes. Nature 446, 153-158 (2007).
10. Schlessinger, J. Cell signaling by receptor tyrosine kinases. Cell 103, 211-225 (2000).
11. Hanahan, D. & Weinberg, R. A. The hallmarks of cancer. Cell 100, 57-70 (2000).
12. Mendel, D. B., et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9, 327-337 (2003).
13. Collins, R. J., Harmon, B. V., Gobe, G. C. & Kerr, J. F. Internucleosomal DNA cleavage should not be the sole criterion for identifying apoptosis. International journal of radiation biology 61, 451-453 (1992).
14. Gold, R., et al. Differentiation between cellular apoptosis and necrosis by the combined use of in situ tailing and nick translation techniques. Laboratory investigation; a journal of technical methods and pathology 71, 219-225 (1994).
15. Brat, D. J., Bellail, A. C. & Van Meir, E. G. The role of interleukin-8 and its receptors in gliomagenesis and tumoral angiogenesis. Neuro-oncol 7, 122-133 (2005).
16. Mizukami, Y., et al. Induction of interleukin-8 preserves the angiogenic response in HIF-1alpha-deficient colon cancer cells. Nat Med 11, 992-997 (2005).
17. Koch, A. E., et al. Interleukin-8 as a macrophage-derived mediator of angiogenesis. Science 258, 1798-1801 (1992).

18. Smith, D. R., et al. Inhibition of interleukin 8 attenuates angiogenesis in bronchogenic carcinoma. J Exp Med 179, 1409-1415 (1994).

19. Huang, D., et al. Inhibition of MAPK kinase signaling pathways suppressed renal cell carcinoma growth and angiogenesis in vivo. Cancer Res 68, 81-88 (2008).

20. O'Farrell, A. M., et al. An innovative phase I clinical study demonstrates inhibition of FLT3 phosphorylation by SU11248 in acute myeloid leukemia patients. Clin Cancer Res 9, 5465-5476 (2003).

21. Faivre, S., et al. Safety, pharmacokinetic, and antitumor activity of SU11248, a novel oral multitarget tyrosine kinase inhibitor, in patients with cancer. J Clin Oncol 24, 25-35 (2006).

22. O'Farrell, A. M., et al. SU11248 is a novel FLT3 tyrosine kinase inhibitor with potent activity in vitro and in vivo. Blood 101, 3597-3605 (2003).

23. Osusky, K. L., et al. The receptor tyrosine kinase inhibitor SU11248 impedes endothelial cell migration, tubule formation, and blood vessel formation in vivo, but has little effect on existing tumor vessels. Angiogenesis 7, 225-233 (2004).

24. Schueneman, A. J., et al. SU11248 maintenance therapy prevents tumor regrowth after fractionated irradiation of murine tumor models. Cancer Res 63, 4009-4016 (2003).

What is claimed is:

1. A method of determining whether a tumor will respond to sunitinib therapy comprising:
   (a) providing a biological sample from a tumor;
   (b) detecting a level of IL-8 expression in the sample;
   (c) comparing the IL-8 level in the sample to a suitable control; and
   determining that an elevated IL-8 expression level in the sample as compared to the control indicates the tumor will not respond to sunitinib therapy.

2. The method of claim 1 wherein the tumor is a renal cell tumor.

3. The method of claim 1 wherein the control is the median or average expression level of IL-8 in tumors of the same tissue type that are not resistant to sunitinib therapy.

4. A method of determining whether a tumor will respond to sunitinib therapy comprising: detecting a level of IL-8 expression in a biological sample from a tumor; and determining that an elevated IL-8 expression level in the sample as compared to a suitable control indicates the tumor will not respond to sunitinib therapy.

5. The method of claim 4 wherein the tumor is a renal cell tumor.

6. The method of claim 4 wherein the control is the median or average expression level of IL-8 in tumors of the same tissue type that are not resistant to sunitinib therapy.

* * * * *

SEQUENCE LISTING

```
<160> NUMBER OF SEQ ID NOS: 4

<210> SEQ ID NO 1
<211> LENGTH: 1666
<212> TYPE: DNA
<213> ORGANISM: Homo sapiens

<400> SEQUENCE: 1
ctccataagg cacaaacttt cagagacagc agagcacaca agcttctagg acaagagcca      60
ggaagaaacc accggaagga accatctcac tgtgtgtaaa catgacttcc aagctggccg     120
tggctctctt ggcagccttc ctgatttctg cagctctgtg tgaaggtgca gttttgccaa     180
ggagtgctaa agaacttaga tgtcagtgca taaagacata ctccaaacct ttccacccca     240
aatttatcaa agaactgaga gtgattgaga gtggaccaca ctgcgccaac acagaaatta     300
ttgtaaagct ttctgatgga agagagctct gtctggaccc caaggaaaac tgggtgcaga     360
gggttgtgga aagttttg aagagggctg agaattcata aaaaaattca ttctctgtgg      420
tatccaagaa tcagtgaaga tgccagtgaa acttcaagca aatctacttc aacacttcat     480
gtattgtgtg ggtctgttgt agggttgcca gatgcaatac aagattcctg gttaaatttg     540
aatttcagta aacaatgaat agtttttcat tgtaccatga aatatccaga acatacttat     600
atgtaaagta ttatttattt gaatctacaa aaaacaacaa ataattttta aatataagga     660
ttttcctaga tattgcacgg gagaatatac aaatagcaaa attgaggcca agggccaaga     720
gaatatccga actttaattt caggaattga atgggtttgc tagaatgtga tatttgaagc     780
atcacataaa aatgatggga caataaattt tgccataaag tcaaatttag ctggaaatcc     840
tggatttttt tctgttaaat ctggcaaccc tagtctgcta gccaggatcc acaagtcctt     900
gttccactgt gccttggttt ctcctttatt tctaagtgga aaaagtatta gccaccatct     960
tacctcacag tgatgttgtg aggacatgtg gaagcacttt aagttttttc atcataacat    1020
aaattatttt caagtgtaac ttattaacct atttattatt tatgtattta tttaagcatc    1080
aaatatttgt gcaagaattt ggaaaaatag aagatgaatc attgattgaa tagttataaa    1140
gatgttatag taaatttatt ttattttaga tattaaatga tgttttatta gataaatttc    1200
aatcagggtt tttagattaa acaaacaaac aattgggtac ccagttaaat tttcatttca    1260
gataaacaac aaataatttt ttagtataag tacattattg tttatctgaa attttaattg    1320
aactaacaat cctagtttga tactcccagt cttgtcattg ccagctgtgt tggtagtgct    1380
gtgttgaatt acggaataat gagttagaac tattaaaaca gccaaaactc cacagtcaat    1440
attagtaatt tcttgctggt tgaaacttgt ttattatgta caaatagatt cttataatat    1500
```

```
tatttaaatg actgcatttt taaatacaag gctttatatt tttaacttta agatgttttt    1560
atgtgctctc caaattttt ttactgtttc tgattgtatg gaaatataaa agtaaatatg     1620
aaacatttaa aatataattt gttgtcaaag taaaaaaaaa aaaaaa                   1666
```

<210> SEQ ID NO 2
<211> LENGTH: 99
<212> TYPE: PRT
<213> ORGANISM: Homo sapiens

<400> SEQUENCE: 2

```
Met Thr Ser Lys Leu Ala Val Ala Leu Leu Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
        50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 3
<211> LENGTH: 1825
<212> TYPE: DNA
<213> ORGANISM: Homo sapiens

<400> SEQUENCE: 3

```
agaaaggaac acagtaaact gaattgatcc gtttagaagt ttacaatgaa gtttcttcta     60
atactgctcc tgcaggccac tgcttctgga gctcttcccc tgaacagctc tacaagcctg    120
gaaaaaaata atgtgctatt tggtgaaaga tacttagaaa aatttttatgg ccttgagata   180 aacaaacttc cagtgacaaa aatgaaatat agtggaaact taatgaagga aaaaatccaa    240
gaaatgcagc acttcttggg tctgaaagtg accgggcaac tggacacatc taccctggag    300
atgatgcacg cacctcgatg tggagtcccc gatgtccatc atttcaggga aatgccaggg    360
gggcccgtat ggaggaaaca ttatatcacc tacagaatca ataattacac acctgacatg    420
aaccgtgagg atgttgacta cgcaatccgg aaagcttttc aagtatggag taatgttacc    480
cccttgaaat tcagcaagat taacacaggc atggctgaca ttttggtggt ttttgcccgt    540
ggagctcatg gagacttcca tgcttttgat ggcaaaggtg aatcctagc ccatgctttt    600 ggacctggat ctggcattgg aggggatgca catttcgatg aggacgaatt ctggactaca    660
cattcaggag gcaccaactt gttcctcact gctgttcacg agattggcca ttccttaggt    720
cttggccatt ctagtgatcc aaaggccgta atgttcccca cctacaaata tgttgacatc    780
aacacatttc gcctctctgc tgatgacata cgtggcattc agtccctgta tggagacca     840 aaagagaacc aacgcttgcc aaatcctgac aattcagaac cagctctctg tgaccccaat    900
ttgagttttg atgctgtcac taccgtggga aataagatct ttttcttcaa agacaggttc    960
ttctggctga aggtttctga gagaccaaag accagtgtta atttaatttc ttccttatgg   1020
ccaaccttgc catctggcat tgaagctgct tatgaaattg aagccagaaa tcaagttttt   1080 cttttttaaag atgacaaata ctggttaatt agcaatttaa gaccagagcc aaattatccc   1140
```

-continued

```
aagagcatac attcttttgg ttttcctaac tttgtgaaaa aaattgatgc agctgttttt    1200
aacccacgtt tttataggac ctacttcttt gtagataacc agtattggag gtatgatgaa    1260
aggagacaga tgatggaccc tggttatccc aaactgatta ccaagaactt ccaaggaatc    1320
gggcctaaaa ttgatgcagt cttctactct aaaaacaaat actactattt cttccaagga    1380
tctaaccaat ttgaatatga cttcctactc caacgtatca ccaaaacact gaaaagcaat    1440
agctggtttg gttgttagaa atggtgtaat taatggtttt tgttagttca cttcagctta    1500
ataagtattt attgcatatt tgctatgtcc tcagtgtacc actacttaga gatatgtatc    1560
ataaaaataa aatctgtaaa ccataggtaa tgattatata aaatacataa tatttttcaa    1620
ttttgaaaac tctaattgtc cattcttgct tgactctact attaagtttg aaaatagtta    1680
ccttcaaagg ccaagagaat tctatttgaa gcatgctctg taagttgctt cctaacatcc    1740
ttggactgag aaattatact tacttctggc ataactaaaa ttaagtatat atattttggc    1800
tcaaataaaa ttgaaaaaaa aatca                                          1825
```

<210> SEQ ID NO 4
<211> LENGTH: 470
<212> TYPE: PRT
<213> ORGANISM: Homo sapiens

<400> SEQUENCE: 4

```
Met Lys Phe Leu Leu Ile Leu Leu Gln Ala Thr Ala Ser Gly Ala
1               5                   10                  15

Leu Pro Leu Asn Ser Ser Thr Ser Leu Glu Lys Asn Asn Val Leu Phe
                20                  25                  30

Gly Glu Arg Tyr Leu Glu Lys Phe Tyr Gly Leu Glu Ile Asn Lys Leu
            35                  40                  45

Pro Val Thr Lys Met Lys Tyr Ser Gly Asn Leu Met Lys Glu Lys Ile
        50                  55                  60

Gln Glu Met Gln His Phe Leu Gly Leu Lys Val Thr Gly Gln Leu Asp
65                  70                  75                  80

Thr Ser Thr Leu Glu Met Met His Ala Pro Arg Cys Gly Val Pro Asp
                85                  90                  95

Val His His Phe Arg Glu Met Pro Gly Gly Pro Val Trp Arg Lys His
            100                 105                 110

Tyr Ile Thr Tyr Arg Ile Asn Asn Tyr Thr Pro Asp Met Asn Arg Glu
        115                 120                 125

Asp Val Asp Tyr Ala Ile Arg Lys Ala Phe Gln Val Trp Ser Asn Val
    130                 135                 140

Thr Pro Leu Lys Phe Ser Lys Ile Asn Thr Gly Met Ala Asp Ile Leu
145                 150                 155                 160

Val Val Phe Ala Arg Gly Ala His Gly Asp Phe His Ala Phe Asp Gly
                165                 170                 175

Lys Gly Gly Ile Leu Ala His Ala Phe Gly Pro Gly Ser Gly Ile Gly
            180                 185                 190

Gly Asp Ala His Phe Asp Glu Asp Glu Phe Trp Thr Thr His Ser Gly
        195                 200                 205

Gly Thr Asn Leu Phe Leu Thr Ala Val His Glu Ile Gly His Ser Leu
    210                 215                 220

Gly Leu Gly His Ser Ser Asp Pro Lys Ala Val Met Phe Pro Thr Tyr
225                 230                 235                 240

Lys Tyr Val Asp Ile Asn Thr Phe Arg Leu Ser Ala Asp Asp Ile Arg
                245                 250                 255
```

-continued

```
Gly Ile Gln Ser Leu Tyr Gly Asp Pro Lys Glu Asn Gln Arg Leu Pro
                260                 265                 270

Asn Pro Asp Asn Ser Glu Pro Ala Leu Cys Asp Pro Asn Leu Ser Phe
        275                 280                 285

Asp Ala Val Thr Thr Val Gly Asn Lys Ile Phe Phe Lys Asp Arg
    290                 295                 300

Phe Phe Trp Leu Lys Val Ser Glu Arg Pro Lys Thr Ser Val Asn Leu
305                 310                 315                 320

Ile Ser Ser Leu Trp Pro Thr Leu Pro Ser Gly Ile Glu Ala Ala Tyr
                325                 330                 335

Glu Ile Glu Ala Arg Asn Gln Val Phe Leu Phe Lys Asp Lys Tyr
                340                 345                 350

Trp Leu Ile Ser Asn Leu Arg Pro Glu Pro Asn Tyr Pro Lys Ser Ile
                355                 360                 365

His Ser Phe Gly Phe Pro Asn Phe Val Lys Lys Ile Asp Ala Ala Val
        370                 375                 380

Phe Asn Pro Arg Phe Tyr Arg Thr Tyr Phe Phe Val Asp Asn Gln Tyr
385                 390                 395                 400

Trp Arg Tyr Asp Glu Arg Arg Gln Met Met Asp Pro Gly Tyr Pro Lys
            405                 410                 415

Leu Ile Thr Lys Asn Phe Gln Gly Ile Gly Pro Lys Ile Asp Ala Val
                420                 425                 430

Phe Tyr Ser Lys Asn Lys Tyr Tyr Tyr Phe Phe Gln Gly Ser Asn Gln
        435                 440                 445

Phe Glu Tyr Asp Phe Leu Leu Gln Arg Ile Thr Lys Thr Leu Lys Ser
    450                 455                 460

Asn Ser Trp Phe Gly Cys
465                 470
```